United States Patent
Kahook et al.

(10) Patent No.: US 11,298,262 B2
(45) Date of Patent: Apr. 12, 2022

(54) OPHTHALMIC DEVICE FOR DRUG DELIVERY

(71) Applicants: The Regents of the University of Colorado, a body corporate, Denver, CO (US); SpyGlass Pharma, Inc., Aliso Viejo, CA (US)

(72) Inventors: Malik Y. Kahook, Denver, CO (US); Glenn Sussman, Aliso Viejo, CA (US); Craig Alan Cable, II, Aliso Viejo, CA (US)

(73) Assignees: THE REGENTS OF THE UNIVERSITY OF COLORADO, A BODY CORPORATE, Denver, CO (US); SPYGLASS PHARMA, INC., Aliso Viejo, CA (US)

( * ) Notice: Subject to any disclaimer, the term of this patent is extended or adjusted under 35 U.S.C. 154(b) by 0 days.

(21) Appl. No.: 16/516,356

(22) Filed: Jul. 19, 2019

(65) Prior Publication Data

US 2020/0022840 A1    Jan. 23, 2020

Related U.S. Application Data

(60) Provisional application No. 62/820,381, filed on Mar. 19, 2019, provisional application No. 62/719,922, (Continued)

(51) Int. Cl.
*A61F 2/16* (2006.01)
*A61F 9/00* (2006.01)
*A61F 2/14* (2006.01)

(52) U.S. Cl.
CPC ............ *A61F 9/0017* (2013.01); *A61F 2/147* (2013.01); *A61F 2/15* (2015.04); *A61F 2/16* (2013.01);
(Continued)

(58) Field of Classification Search
CPC .................................................. A61F 2002/169
See application file for complete search history.

(56) References Cited

U.S. PATENT DOCUMENTS 5,074,876 A    12/1991   Kelman
5,628,795 A     5/1997   Langerman
(Continued)

FOREIGN PATENT DOCUMENTS

EP    1543799        6/2005
EP    3210572 A1    8/2017
(Continued)

OTHER PUBLICATIONS

Clara González-Chomón, et al. "Drug-Eluting Intraocular Lenses" Materials, Nov. 1, 2011, pp. 1927-1940, vol. 4.
(Continued)

*Primary Examiner* — Leslie Lopez
(74) *Attorney, Agent, or Firm* — Polsinelli PC

(57) ABSTRACT

An ophthalmic implant for drug delivery. The implant includes a primary intracapsular device coupled to a secondary device, wherein, when implanted in a patient's eye, the primary intracapsular device is held in place by the patient's capsular bag and the secondary device is held in place by the primary intracapsular device. The implant may be inserted in the eye by injecting the primary intracapsular device into the eye either before or after attaching the secondary device to the primary intracapsular device, and subsequently positioning the joined secondary device and primary intracapsular device with the primary intracapsular device held in place by the patient's capsular bag and the secondary device held in place by the primary intracapsular device. The secondary device may be designed to hold a tertiary device that can be implanted and attached at the time of surgery or anytime postoperatively.

7 Claims, 23 Drawing Sheets

Related U.S. Application Data filed on Aug. 20, 2018, provisional application No. 62/702,169, filed on Jul. 23, 2018.

(52) U.S. Cl.
CPC . *A61F 2002/169* (2015.04); *A61F 2002/1683* (2013.01); *A61F 2002/1689* (2013.01); *A61F 2002/1699* (2015.04); *A61F 2002/16905* (2015.04); *A61F 2220/0033* (2013.01); *A61F 2230/0065* (2013.01); *A61F 2250/0063* (2013.01); *A61F 2250/0067* (2013.01)

(56) References Cited

U.S. PATENT DOCUMENTS

| | | | |
|---|---|---|---|
| 7,713,299 | B2 | 5/2010 | Brady et al. |
| 8,652,206 | B2 | 2/2014 | Masket |
| 8,663,235 | B2 | 3/2014 | Tassignon |
| 8,728,158 | B2 | 5/2014 | Whitsett |
| 9,358,103 | B1 | 6/2016 | Wortz et al. |
| 9,999,595 | B2 | 6/2018 | Rakic et al. |
| 2003/0149479 | A1 | 8/2003 | Snyder et al. |
| 2006/0047339 | A1 | 3/2006 | Brown |
| 2007/0026042 | A1* | 2/2007 | Narayanan ............... A61L 27/34 424/426 |
| 2007/0123981 | A1 | 5/2007 | Tassignon |
| 2009/0130176 | A1 | 5/2009 | Bossy-Nobs et al. |
| 2010/0204790 | A1 | 8/2010 | Whitsett |
| 2011/0125090 | A1 | 5/2011 | Peyman |
| 2011/0282328 | A1 | 11/2011 | Ambati et al. |
| 2011/0313521 | A1 | 12/2011 | Angelopoulos |
| 2013/0190868 | A1* | 7/2013 | Kahook ............... A61F 2/1648 623/6.41 |
| 2014/0148900 | A1* | 5/2014 | Ratner ................. A61K 31/711 623/6.43 |
| 2014/0288645 | A1* | 9/2014 | Cuevas ............... A61L 27/3869 623/6.16 |
| 2015/0209274 | A1* | 7/2015 | Venkatraman ........ A61F 9/0017 424/427 |
| 2015/0238309 | A1 | 8/2015 | Jansen |
| 2015/0342729 | A1 | 12/2015 | Kahook et al. |
| 2016/0256262 | A1 | 9/2016 | Wortz et al. |
| 2016/0331519 | A1 | 11/2016 | Kahook et al. |
| 2017/0119521 | A1* | 5/2017 | Kahook ................ A61F 2/1648 |
| 2017/0296331 | A1* | 10/2017 | Werblin ................ A61F 2/1664 |
| 2018/0014928 | A1 | 1/2018 | Kahook et al. |
| 2018/0368974 | A1* | 12/2018 | Kahook ................ A61F 2/1648 |

FOREIGN PATENT DOCUMENTS

| | | |
|---|---|---|
| KR | 20160045129 A | 4/2016 |
| WO | WO 2008/094518 | 8/2008 |
| WO | WO 2008/113043 | 9/2008 |
| WO | 2016062503 A2 | 4/2016 |
| WO | WO 2018/064578 | 4/2018 |
| WO | 2018078026 A1 | 5/2018 |
| WO | 2018125930 A1 | 7/2018 |

OTHER PUBLICATIONS

Yu-Chi Liu, et al. "Intraocular Lens as a Drug Delivery Reservoir" Cataract Surgery and Lens Implantation, Wolters Kluwer Health, Jan. 2013, pp. 53-39, vol. 24, No. 1, Lippincott Williams & Wilkins.

Bahram Resul, et al. "Structure-Activity Relationships and Receptor Profiles of Some Ocular Hypotensive Prostanoids" Survey of Ophthalmology, Feb. 1997, pp. S47-S52, vol. 41, supp. 2.

Johan Wilhelm Stjernschantz "From PGF2α-Isopropyl Ester to Latanoprost A Review of the Development of Xalatan the Proctor Lecture" Investigative Ophthalmology & Visual Science, May 2001, pp. 1134-1145, vol. 42.

International Application No. PCT/US2019/042515, International Search Report & Written Opinion, 10 pages, Oct. 2, 2019.

* cited by examiner

OPHTHALMIC DEVICE FOR DRUG DELIVERY

CROSS-REFERENCE

This application claims the benefit of U.S. Provisional Application No. 62/820,381, filed Mar. 19, 2019, U.S. Provisional Application No. 62/719,922, filed Aug. 20, 2018, and U.S. Provisional Application No. 62/702,169, filed Jul. 23, 2018, which applications are incorporated herein by reference.

BACKGROUND

An ophthalmic device can be implanted in a patient's eye to treat, diagnose, monitor or otherwise benefit ophthalmic or systemic diseases or conditions. For example, after cataract removal or other intraocular surgery, an intraocular device may be implanted in the eye to deliver steroids, NSAIDS, or antibiotics. An intraocular device may also be implanted in the eye to deliver long-term drugs, such as in the treatment of glaucoma. Alternatively, an intraocular device may mechanically alter the light transmittance into the patient's eye in the treatment of astigmatism, for example, or to enhance vision, or the intraocular device may act as an artificial iris in certain cases.

There are drawbacks associated with such existing ophthalmic devices, including injury to ocular tissues relating to device migration. If an ophthalmic device is not properly stabilized, this can lead to anterior capsular opacification, loss of capsule integrity, deformation of the shape of the capsulotomy, phimosis of the capsulotomy over time, tilt and decentration of the lens, and other undesirable effects.

There is a need or desire for an intraocular device that can be implanted in a patient's eye that minimizes damage to collateral tissues. There is a further need or desire for an intraocular device that can be implanted in a patient's eye that provides lens stability.

SUMMARY

An ophthalmic implant, as described herein, includes a primary intracapsular device coupled to a secondary device, wherein, when implanted in a patient's eye, the primary intracapsular device is held in place by the patient's capsular bag and the secondary device is held in place by the primary intracapsular device. Both the primary intracapsular device and the secondary device may be positioned inside the capsular bag in the patient's eye. Alternatively, the primary intracapsular device may be positioned inside the capsular bag while the secondary device may be positioned outside the capsular bag in the patient's eye, with the patient's anterior capsule or a portion of the patient's anterior capsule positioned between the primary intracapsular device and the secondary extracapsular device. The secondary device may be designed to hold a tertiary device that can be implanted either at the time of initial surgery or any time thereafter. The insertion of the ophthalmic implant into the patient's eye may lead to partial or full compression of the anterior capsule against the primary intracapsular device, which provides substantial lens stability.

The primary intracapsular device may be an intraocular lens, a capsular tension ring, or a capsular scaffold for holding the secondary device in place. The secondary device may be in the form of a ring or one or more partial rings or protrusions, for example. The secondary device may be secured to one or more extensions extending from the primary device. Alternatively, the primary device may be secured to one or more extensions extending from the secondary device.

The secondary device may be a drug delivery device that delivers one or more active pharmaceutical ingredients that can treat ocular disease. The secondary device may include a sheath that houses one or more drug delivery devices and one or more drugs. Additionally or alternatively, the secondary device may be an optical mask that can control the amount of light that enters a patient's eye.

The tertiary device may be in the form of a ring or one or more partial rings, for example, and may include a sheath that houses one or more drug delivery devices and one or more drugs. The tertiary device may deliver drugs, function as an artificial iris, or resolve dysphotopsia. Additionally or alternatively, the tertiary device may be an optical mask that can control the amount of light that enters a patient's eye.

A method of addressing ocular disease using an ophthalmic implant, as described herein, includes injecting the primary intracapsular device and the secondary device into the eye either before or after attaching the secondary device to the primary intracapsular device. As described above, the joined primary intracapsular device and secondary device may both be positioned inside the capsular bag in the patient's eye, with the secondary intracapsular device positioned between the patient's anterior capsule and the primary intracapsular device. Alternatively, the primary intracapsular device may be positioned inside the capsular bag while the secondary device may be positioned outside the capsular bag in the patient's eye, with the patient's anterior capsule or a portion of the patient's anterior capsule positioned between the primary intracapsular device and the secondary extracapsular device. Furthermore, a tertiary device may be implanted and attached at the time of surgery or anytime postoperatively.

BRIEF DESCRIPTION OF THE DRAWINGS

In order to describe the manner in which the above-recited and other advantages and features can be obtained, a more particular description is set forth and will be rendered by reference to specific examples thereof which are illustrated in the appended drawings. Understanding that these drawings depict only typical examples and are not therefore to be considered to be limiting of its scope, implementations will be described and explained with additional specificity and detail through the use of the accompanying drawings.

Figure 1:
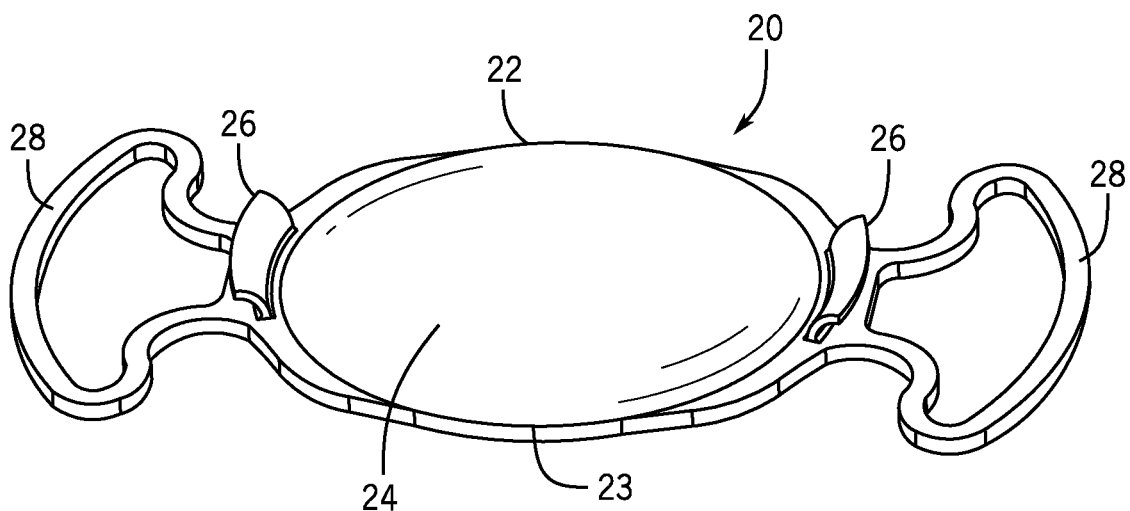
FIG. 1 is a perspective view of an intraocular lens with supracapsular extensions.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

An ophthalmic device, as described herein, can be implanted in a patient's eye to treat, diagnose, monitor or otherwise benefit ophthalmic or systemic diseases or conditions. The ophthalmic device includes a primary device coupled to a secondary device. In each of the embodiments, the primary device is implanted in the patient's capsular bag. While the primary intracapsular device is held in place by the capsular bag, the secondary capsular device is held in place, at least in part, by the primary intracapsular device. A tertiary device may be held in place by the secondary device and can be fully within the capsular bag, partially in and partially out of the capsular bag, or fully above the capsular bag.

According to one embodiment, the primary intracapsular device is positioned inside the patient's capsular bag, and a secondary device is a secondary extracapsular device that is positioned outside the patient's capsular bag in the patient's eye. The primary intracapsular device may be tethered to the secondary extracapsular device with the secondary extracapsular device transitioning from intracapsular attachment(s) to the supracapsular plane. When implanted in the patient's eye, the primary intracapsular device is held in place by the patient's capsular bag and the secondary extracapsular device is held in place by the primary intracapsular device, with the patient's anterior capsule or a portion thereof positioned between the primary intracapsular device and the secondary extracapsular device. The secondary extracapsular device may be at least partially held in place by the anterior capsule. The positioning of the ophthalmic implant in the patient's eye may lead to partial or full compression of the anterior capsule or portion thereof against the primary intracapsular device, which provides substantial lens stability.

By holding the secondary extracapsular device in place above the anterior capsule of the lens bag in the patient's eye, the ophthalmic device may also provide spacing between the secondary extracapsular device and the iris, ciliary sulcus tissue, and/or zonules. This positioning of the secondary extracapsular device prevents chafing or other discomfort caused by friction between the secondary extracapsular device and the eye tissues. The placement of the secondary extracapsular device can also reduce or prevent intraocular lens edge-related positive and negative dysphotopsias by stabilizing a capsulotomy, thus eliminating optical effects from the capsulotomy edge or the intraocular lens edge. The extensions in combination with the secondary extracapsular device may also act as a reservoir to hold a drug in place with or without control of elution rate.

According to another embodiment, a primary intracapsular device is positioned inside the patient's capsular bag, and a secondary device is a secondary intracapsular device that is joined to the primary intracapsular device and is also positioned inside the patient's capsular bag in the patient's eye. A tertiary device may be held in place by the secondary intracapsular device and can be fully within the capsular bag, partially in and partially out of the capsular bag, or fully above the capsular bag. More particularly, the secondary intracapsular device is positioned between the primary intracapsular device and the anterior capsule of the patient's eye within the capsular bag. In this manner, the intraocular device is positioned to receive the tertiary device without having to manipulate the primary intracapsular device or the secondary intracapsular device. Unless specified, the secondary devices described in the embodiments below may be either intracapsular secondary devices or extracapsular secondary devices.

According to certain embodiments, as shown in FIG. 1, the intraocular device 20 includes a primary intracapsular device 23 in the form of an intraocular lens 22 or optic. As described in greater detail below, as an alternative, the primary intracapsular device 23 may be a device other than an intraocular lens. For example, the primary intracapsular device 23 may be a capsular tension ring, or a capsular scaffold. Various configurations can be used to join the secondary device to the primary intracapsular device 23. As shown in the embodiment in FIG. 1, the primary intracapsular device 23 may be equipped with one or more extensions 26 extending from an anterior side 24 of the intraocular lens 22. These extensions 26 may be used to join the secondary device to the primary intracapsular device 23.

The intraocular lens 22 may be held in place in a lens bag of a patient's eye with an intraocular lens haptic 28 or any other suitable attachment device. Once the intraocular lens 22 is implanted in the patient's eye, the one or more extensions 26 extending from the anterior side 24 of the intraocular lens 22 are each at least partially intracapsular and may terminate either below or above a position of an anterior capsule of the lens bag in the patient's eye. In embodiments in which the one or more extensions 26 terminate above a position of an anterior capsule of the lens bag, each of the one or more extensions 26 may also be partially supracapsular.

One or more extensions may extend from the primary intracapsular device to engage the secondary extracapsular device, thereby sandwiching the anterior capsule between the primary intracapsular device and the secondary extracapsular device. If the anterior capsule were not sandwiched in this manner, the anterior capsule may deform at the supracapsular pressure points, which could lead to anterior capsular opacification, loss of capsulotomy integrity, deformation of the shape of the capsulotomy, phimosis of the capsulotomy over time, tilt and decentration of the lens, and other possible unfavorable side effects. Furthermore, the positioning of the primary intracapsular device and the secondary extracapsular device, in combination, may stabilize a capsulotomy. More particularly, compressing the capsulotomy edge between the primary intracapsular device and the secondary extracapsular device allows for stability of the capsulotomy edge with prevention of phimosis while acting as a barrier to cellular proliferation from the anterior capsule to the anterior surface of the optic.

One or more extensions may extend from the primary intracapsular device to engage the secondary intracapsular device, thereby joining the primary intracapsular device to the secondary intracapsular device, with the secondary intracapsular device positioned between the primary intracapsular device and an anterior capsule of the lens bag. A tertiary device may be held in place by the secondary device and can be fully within the capsular bag between the secondary intracapsular device and the anterior capsule of the lens bag, partially in and partially out of the capsular bag, or fully above the capsular bag.

As alternatives to the embodiments described above, rather than the extensions 26 extending from the intraocular lens 22, the one or more extensions 26 may extend from the secondary device 30 device to engage the primary intracapsular device 23.

The extensions 26 may be in the form of tabs, hooks, pegs, rings, a planar surface with indentations, pins, polygons, or other configurations adapted to receive a secondary extracapsular device or a secondary intracapsular device, or if extending from a secondary device, adapted to receive a primary intracapsular device. As shown in FIG. 1, the extensions 26 may be tabs, in this case diametrically opposite one another, facing away from a center of the intraocular lens 22. Alternatively, the extensions 26 may be tabs or indentations that face toward the center of the intraocular lens 22 (not shown). According to certain embodiments, the extensions 26 may be deformable to allow for easier manipulation when attaching the secondary extracapsular or intracapsular device. Flexibility in the extensions 26 can also be beneficial during insertion of the intraocular device 20 into the patient's eye, such that in certain embodiments the primary intracapsular device 23 can be folded and the extensions 26 can hold the primary intracapsular device 23 in the folded position for easier insertion.

Figure 2:
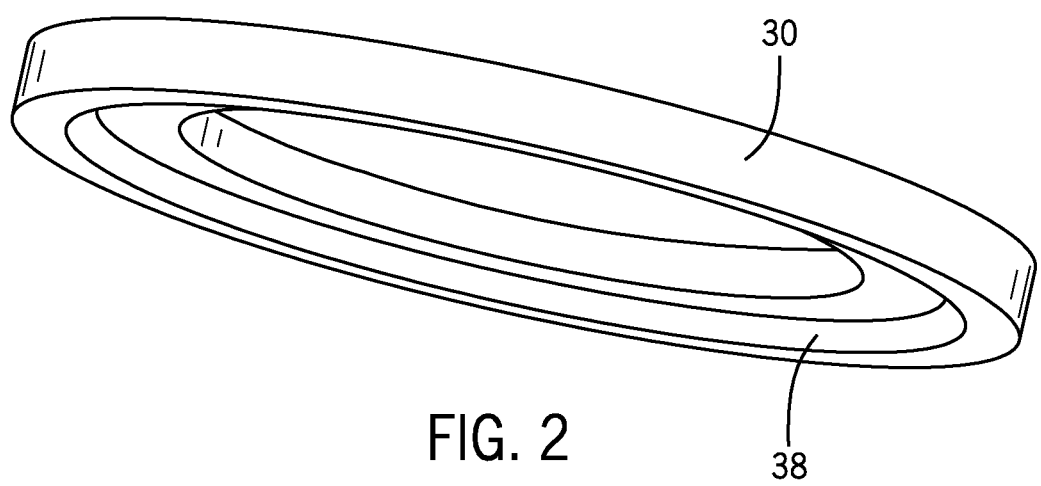
FIG. 2 is a perspective view of a secondary device that can be affixed to the supracapsular extensions in FIG. 1.

A secondary device 30, as shown in FIG. 2, may be affixed to the primary intracapsular device 23. As described above, the secondary device 30 may be positioned above the anterior capsule of the lens bag in the patient's eye, such that the secondary extracapsular device 30 and the extensions 26 reside above the lens bag. The secondary extracapsular device 30 may contact the anterior capsule or be positioned just above the anterior capsule without contacting any structure other than the extensions 26, wherein any other structure refers to the iris, ciliary sulcus tissue, and/or zonules. In particular, the secondary device 30 may be affixed to one or more tabs positioned outside of a visual axis of the intraocular lens 22. The secondary extracapsular or intracapsular device 30 may be non-permanently attached to the extensions 26 such that the secondary device 30 may be replaced as desired or as needed. According to certain embodiments, the secondary device 30 may be biodegradable.

The secondary extracapsular or intracapsular device 30 may be virtually any device affixed anterior or posterior to the lens capsule to treat, diagnose, monitor or otherwise benefit ophthalmic or systemic diseases or conditions. The secondary device 30 can perform optic functions, including refraction correction and presbyopia correction, such as providing extended depth of focus. For example, the secondary device 30 may be a drug delivery device, an optical mask, a pinhole mask, a refractive mask, a toric mask, a multifocal mask, a trifocal mask, an opaque light-blocking surface, a partial light-blocking surface, and/or a dyspho ring. In certain cases, the secondary device 30 may act as an artificial iris, such as in cases of trauma to the iris, or in cases of albinism or aniridia, for example. The secondary device 30 may be any suitable form, such as a ring, a partial ring or ring segment, multiple ring segments, or a polygon.

In one embodiment, the secondary device 30 may be inserted into the eye and positioned over the anterior capsule 36 with one or more extensions 26 going under the anterior capsule 36 to stabilize the secondary device 30 in place prior to injecting a primary intracapsular device 23 through the opening of the secondary device 30 directly into the capsular bag. In this embodiment, the primary intracapsular device 23 may further secure the secondary device 30 within the supracapsular space through one or more supracapsular or intracapsular extensions 26.

As another technique to assist in installing the secondary device 30 on the intraocular lens 22 or scaffold, the extensions 26 and the secondary device 30 may be color-coded to assist in proper positioning. More particularly, when the extensions 26 and the secondary device 30 are color-coded, the secondary device 30 can be positioned onto the extensions 26 to either reveal or conceal a specific color that indicates proper positioning of the secondary device 30 to the supracapsular portions of the extensions 26. According to certain embodiments, other portions of the primary intracapsular device 23, instead of or in addition to the extensions 26, may be color-coded along with the secondary device 30 to assist with proper visualization and positioning of the secondary device 30 with respect to the primary intracapsular device 23.

Figure 3:
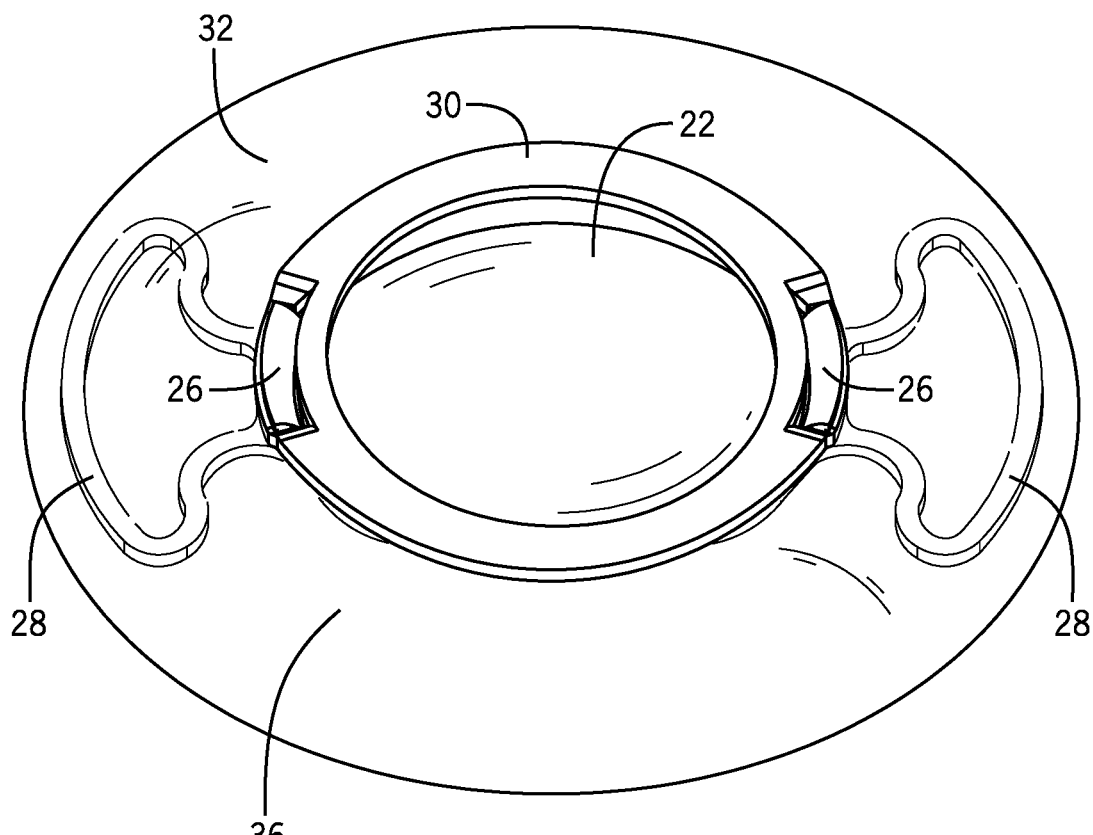
FIG. 3 is a perspective view of one embodiment of an intraocular device attached to a lens bag.

FIG. 3 shows the secondary extracapsular device 30 affixed to the extensions 26 above the anterior capsule of the lens bag 32, while the intraocular lens 22 and haptics 28 reside inside the lens bag 32. The attached secondary extracapsular device 30 may reside along the remaining anterior capsule 36, post creation of a 4.5 mm to 7 mm capsulotomy, of the lens bag 32 after the intraocular lens 22 has been implanted and the extensions 26 positioned over the anterior capsule 36. Attaching the secondary extracapsular device 30 to the intraocular lens 22 may compress the secondary extracapsular device 30 against the anterior capsule 36, with the anterior capsule 36 compressed between the secondary extracapsular device 30 and the intraocular lens 22, which may create an enhanced barrier to anterior capsular opacification (ACO).

Additionally, the primary intracapsular device 23 and/or the secondary extracapsular or intracapsular device 30 may contain fenestrations or openings that allow for evacuation of the viscoelastic from the capsular bag 32 at the conclusion of surgery. Without such fenestrations or passageways, the viscoelastic may displace the lens and cause refractive surprises. In addition to providing an evacuation route for the viscoelastic to exit the capsular bag 32 at the conclusion of surgery, such fenestrations or holes may serve to increase the surface area of the secondary device 30 in order to tune the drug elution when the secondary device 30 is a drug delivery device.

Figure 4:
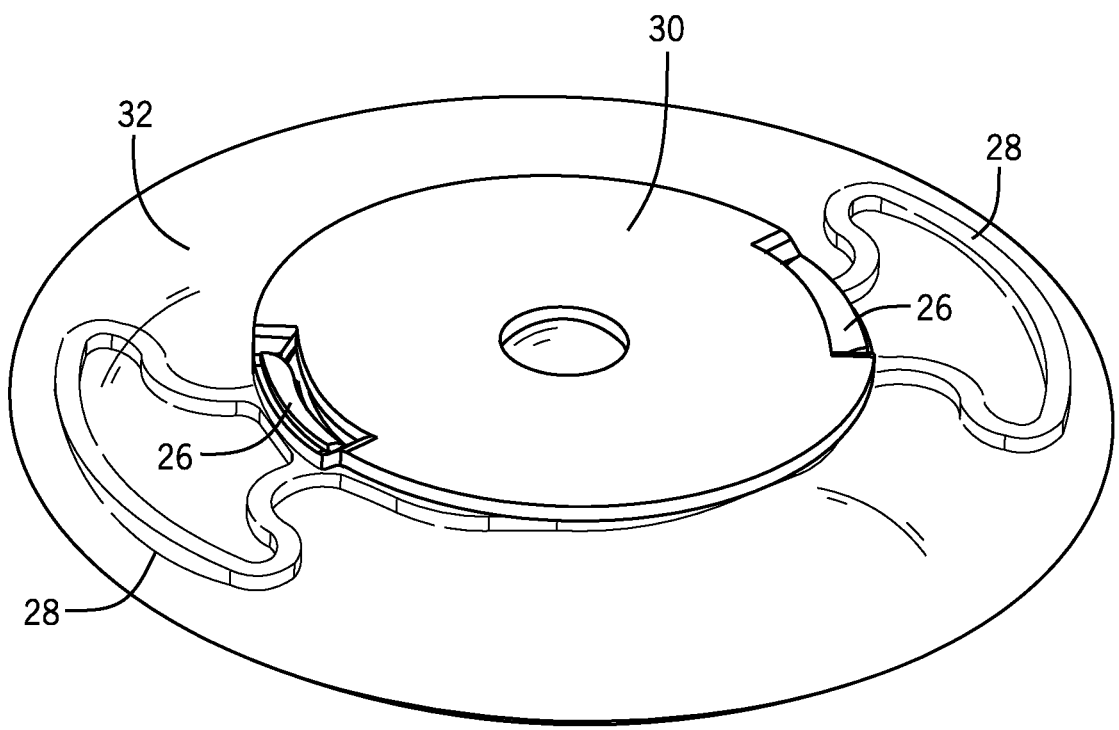
FIG. 4 is a perspective view of another embodiment of an intraocular device attached to a lens bag.

In FIG. 4, the secondary extracapsular device 30 is a pinhole mask. According to certain embodiments, the pinhole can be turned on and off, such that the pinhole may provide a partial or 0% light transmittance pinhole to reduce the effects of astigmatism. Also according to certain embodiments, when a pinhole mask is placed over an implanted intraocular lens 22, the mask may be movable in the x,y plane to position the pinhole over an optimal site in relation to the center of the pupil. The mask may be removed in the case of retinal surgery if the pinhole blocks the view. The pinhole may also be composed of a material that is transparent to non-visible light (infrared light for example) so that scanning imaging devices commonly used in ophthalmology, namely optical coherence tomography imaging (OCT), can still image the posterior pole through the mask. According to some embodiments, the materials used for the primary intracapsular device 23 and/or the secondary device 30 may each include a material that is partially or fully opaque to OCT imaging to assist with image-guided docking.

Figure 5:
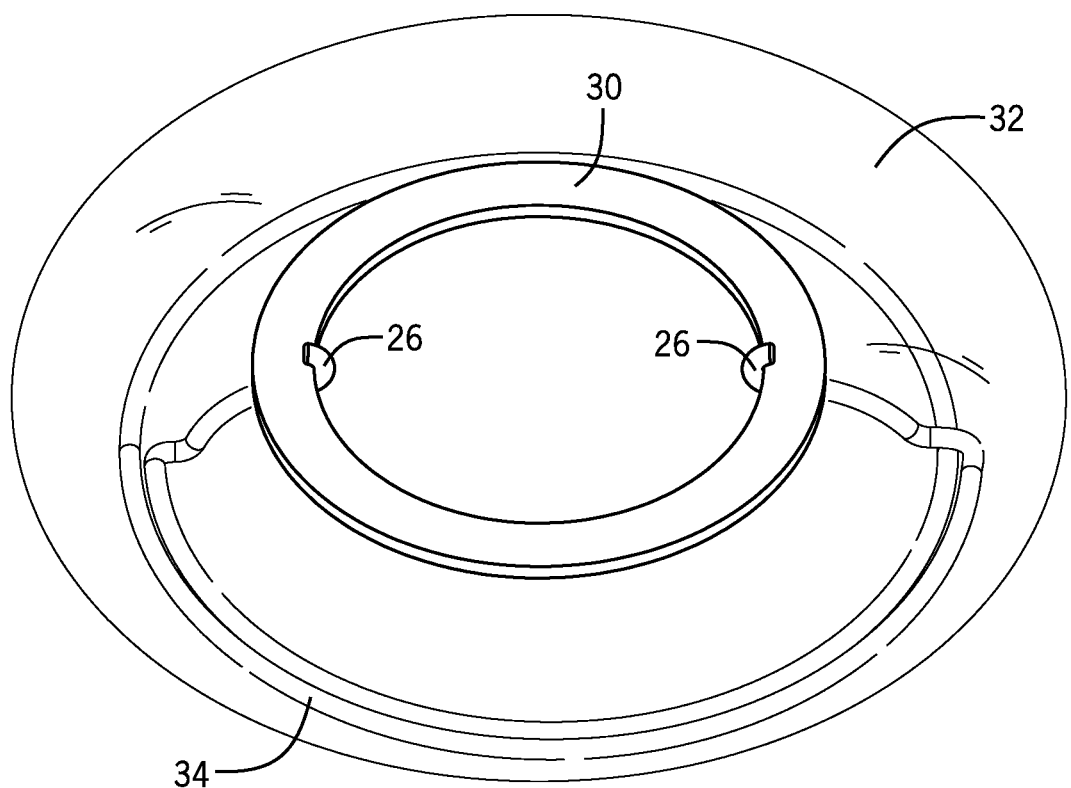
FIG. 5 is a perspective view of yet another embodiment of an intraocular device attached to a lens bag.
Figure 6:
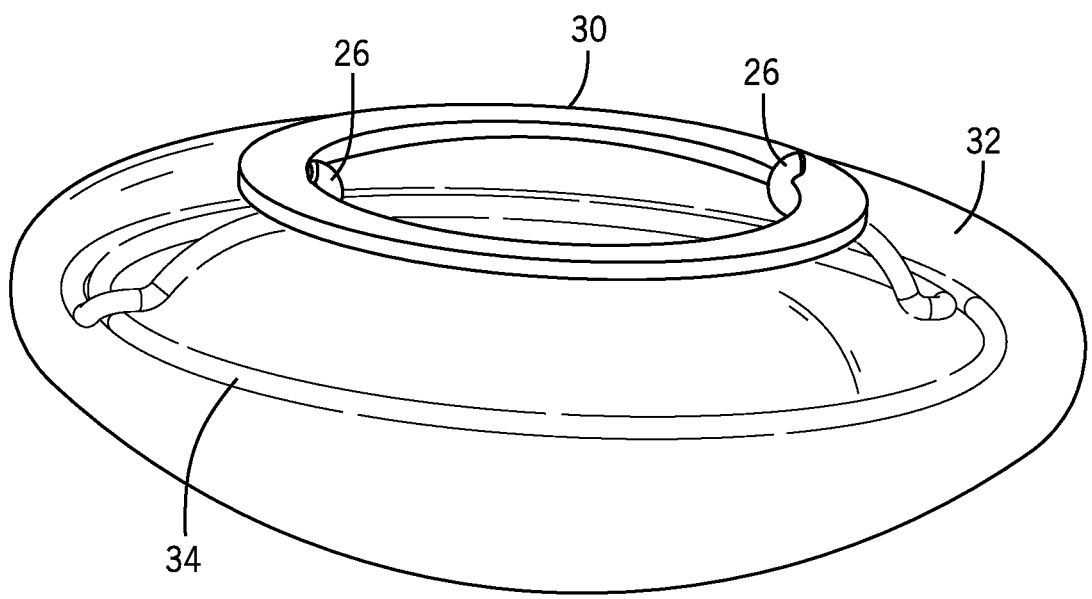
FIG. 6 is another perspective view of the intraocular device in FIG. 5.
Figure 7:
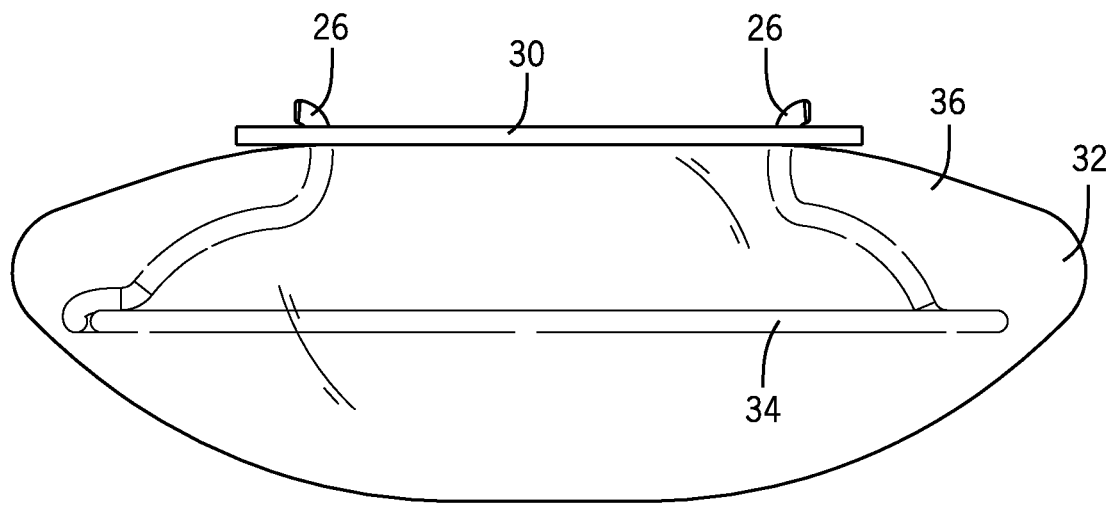
FIG. 7 is a side view of the intraocular device in FIGS. 5 and 6.

FIGS. 5, 6, and 7 show various views of one embodiment of the intraocular device 20 implanted in a lens bag 32. In this embodiment, the primary intracapsular device 23 is a one-piece mechanism that forms an intracapsular scaffold 34 with supracapsular extensions 26. The scaffold 34 may be formed of one piece, as shown, or may be formed of multiple pieces. As shown in the drawings, an intraocular lens may be omitted, with the intracapsular scaffold 34 and its supracapsular extensions 26 affixing the secondary device 30 in place. According to certain embodiments, the scaffold 34 may reside entirely within the sulcus. In another embodiment, a capsular tension ring may also serve as the intracapsular scaffold 34, from which supracapsular extensions 26 may extend. In yet another embodiment, the secondary device 30, which may be a drug delivery device, may be attached to a sulcus fixated ring, sulcus fixated optic, or similar device, so that the entire device resides within the ciliary sulcus plane without extending into the capsular bag 32.

In the side view of FIG. 7, one can clearly see the anterior capsule 36 of the lens bag 32, with the supracapsular extensions 26 extending above the anterior capsule 36 and holding the secondary device 30 in place above the anterior capsule 36 while the intraocular scaffold 34 is positioned within the lens bag 32.

Figure 8:
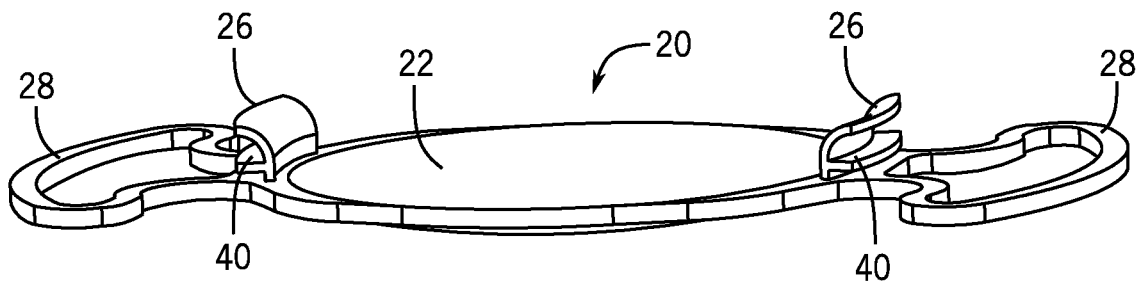
FIG. 8 is a perspective view of another embodiment of an intraocular lens with extensions.
Figure 9:
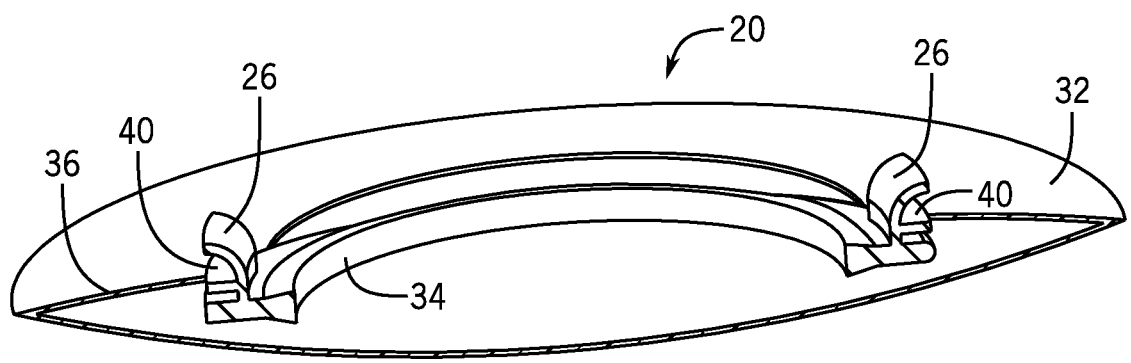
FIG. 9 is a section view of still another embodiment of an intraocular lens with extensions.

The secondary extracapsular or intracapsular device 30, such as in the form of a ring or partial ring, may include one or more ridges 38 on the inside surface or on the outside surface, or micro-patterns, that help secure the secondary device 30 into place on the extensions 26. For example, micro-patterns on the secondary device 30 may attach to corresponding micro-patterns on the extensions 26. Additionally, or alternatively, the extensions 26 may include one or more step features 40, as shown in FIG. 8, that help secure the extensions 26 to the secondary device 30. The embodiment illustrated in FIG. 8 is identical to the embodiment shown in FIG. 1, but with the addition of an additional step feature 40 on the extensions 26. In particular, the additional step feature 40 in FIG. 8 assists in keeping the secondary device 30 spaced apart from the anterior capsule 36 of the lens bag 32. The anterior capsule 36 may be positioned under this step feature 40, as shown in FIG. 9. Alternatively, the step feature 40 may be positioned under the anterior capsule 36. This step feature 40 may reside only under the extension 26 or continue around the intraocular device 20 for 360 degrees, or any portion. According to certain embodiments, ridges and/or micro-patterns may be present on any surface of the extensions 26 and/or the secondary device 30 to help secure the extensions 26 to the secondary device 30.

FIG. 9 is a cross-sectional view of the intraocular device 20 attached to a lens bag 32. In this embodiment, the intraocular scaffold 34 interfaces with the anterior capsule 36 attached within the capsulotomy or capsulorhexis. The intraocular scaffold 34 is open in the middle, with no lens. As indicated above, the feature 40 above the anterior capsule serves to keep the secondary device 30 from contacting the anterior capsule 36, thereby eliminating any potential for adhesion.

According to certain embodiments, micro-patterned surfaces may be present on the secondary device 30 and/or on the intraocular lens 22 and/or on the intraocular scaffold 34 to decrease the surface area available to contact the anterior capsule 36. A micro-pattern on the secondary device 30 may also allow for increased surface area from which to elute a drug. More particularly, the use of micro-patterns on the secondary device 30 is a way to tune release rate of drugs when the secondary device 30 is a drug delivery device.

In one embodiment, the anterior extensions 26 from the intraocular lens 22 or scaffold 34 to the anterior capsule 36 leads to the secondary device 30 being positioned between the anterior capsule 36 and the iris without touching anything but the anterior extensions 26 from the intraocular lens 22 or scaffold 34.

Figure 10:
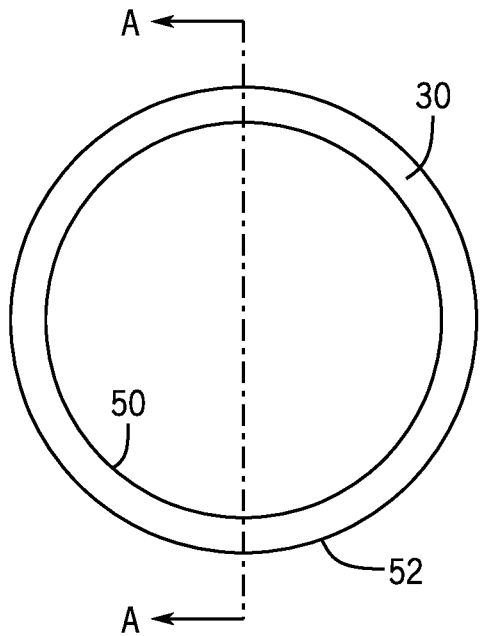
FIG. 10 is a plan view of a secondary device in the form of a ring.
Figure 11:
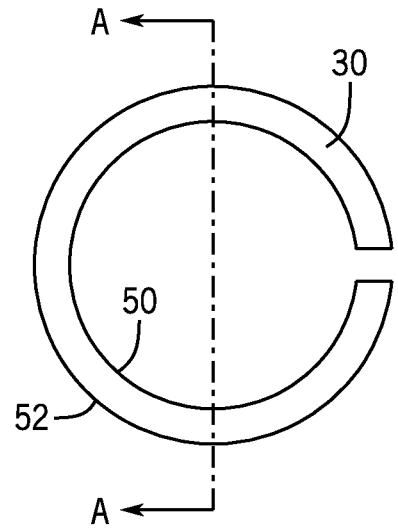
FIG. 11 is a plan view of a secondary device in the form of a partial ring.
Figure 12:
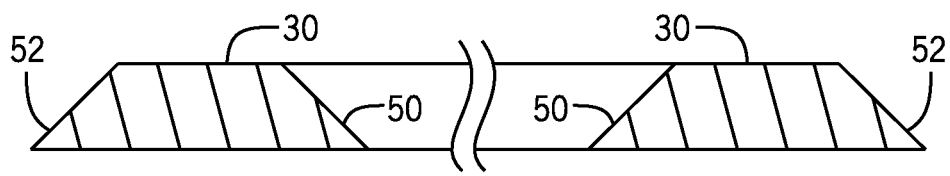
FIG. 12 is a cross-sectional view of either FIG. 10 or FIG. 11.

The secondary device 30 may be in the form of a ring, as shown in FIG. 10, or a partial ring, as shown in FIG. 11, or one or more ring segments. A cross-sectional view of an embodiment of the secondary device 30 taken along line A-A of either FIG. 10 or FIG. 11 is shown in FIG. 12, not necessarily to scale.

One benefit of using a partial ring or ring segment as the secondary device 30, rather than a full ring, is that the partial ring can be more easily manipulated both when installing and removing the secondary device 30. More particularly, the partial ring can be wrapped into place on the extensions 26, rather than having to be stretched over or compressed under the extensions 26 as may be required with a full ring. Also, when using a partial ring or ring segment as the secondary device 30, rather than a full ring, the partial ring can be detached from the extensions 26 by grasping one free end and directing the ring away from the extensions 26, essentially unwinding the device to free the device from the extensions 26 without the need to stretch or compress the device in order to displace it. This would be less traumatic than removing a full ring, and would lead to less movement of the optic in the process of exchanging the ring when drug elution is complete thus requiring a new ring to be installed.

The ring or partial ring may contain a nitinol wire or prolene suture material, which allows the ring to be wrapped into place reliably. More particularly, the nitinol wire or prolene suture material can direct folding and unfolding of the ring to enhance connection with the primary intraocular device. This can take the form of biasing the ring towards bending in one direction when compressed or stretched. Thus, the nitinol wire or prolene suture material enhances positioning of the secondary device 30 on the supracapsular extensions 26.

According to certain embodiments, the secondary device 30 may have one or more indentations or other pre-formed areas that help with bending or folding and unfolding the secondary device 30 in a controlled manner at specific points along a body of the secondary device 30 in relation to installing the secondary device 30 relative to the extensions 26 and/or the primary intracapsular device 23.

As another technique for controlling the bending or folding and unfolding of the intraocular device 20 during insertion, the primary intracapsular device 23 and the secondary device 30 may be made out of different materials that unfold at different rates. This material difference facilitates placement of the primary intracapsular device 23 in the bag and the secondary extracapsular device 30 outside of the bag. Suitable materials include essentially any polymer material suitable for implantation into the eye, including but not limited to acrylic and non-acrylic polymers, silicone materials, and hydrogels. The materials may be hybrid hydrophobic, hydrophilic, or various polymers in different ratios to effect the appropriate modulus needed for the specific application.

The thickness of the secondary device 30 may taper toward an inner diameter 50 of the ring or partial ring, as shown in FIG. 12. Similarly, the thickness of the secondary device 30 may taper toward an outer diameter 52 of the ring or partial ring, as shown in FIG. 12, to avoid the iris tissue, which drapes over this area during normal iris movements. As shown in FIG. 12, the thickness of the ring or partial ring may taper from a central portion of the body to both the inner diameter 50 and the outer diameter 52, with the thickness of the secondary device 30 being smallest along the inner diameter 50 and the outer diameter 52, and the thickness of the secondary device 30 being greatest between the inner diameter 50 and the outer diameter 52 of the ring or partial ring. This wedge shape allows the secondary device 30 to slide in to an optic fixation point on the primary intracapsular device 23 or extensions since the narrowest part of the inner diameter 50 or outer diameter 52 of the ring or partial ring, depending on whether a corresponding wedge of the extensions is facing inward or outward, will go in the widest opening in the wedge of the extensions 26, as shown in FIGS. 13-21. The complementary wedge shapes also cinch down the anterior capsule 36 to the primary intracapsular device 23 or optic more reliably than certain non-wedged configurations.

Figure 13:
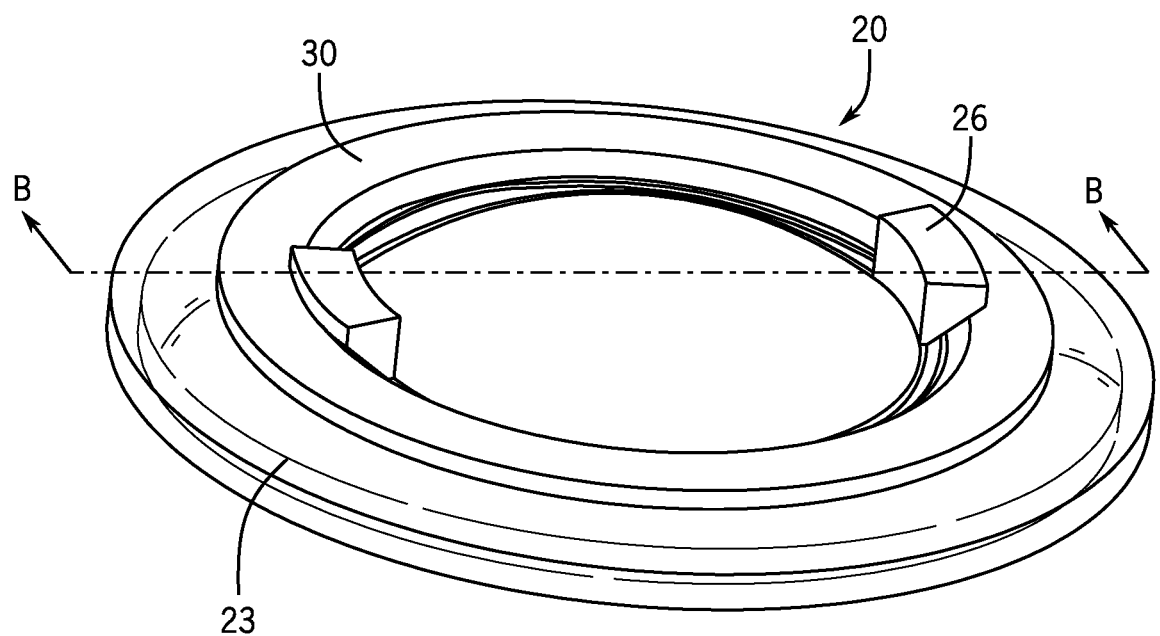
FIG. 13 is a perspective view of another embodiment of an intraocular device.
Figure 14:
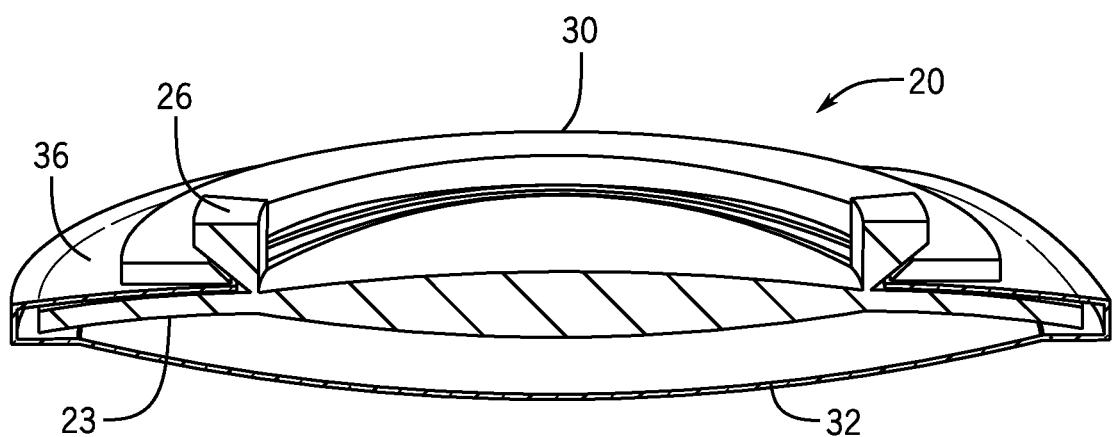
FIG. 14 is a cross-sectional view of FIG. 13.

FIG. 13 shows the intraocular device 20 with the secondary device 30 positioned in place on the primary intracapsular device 23 and secured with the supracapsular extensions 26. FIG. 14 is a cross-sectional view of the intraocular device 20 of FIG. 13 taken along line B-B. FIGS. 15-21 are cross-sectional plan views of various embodiments of the intraocular device 20 of FIG. 13 taken along line B-B. In each of these embodiments, the secondary device 30 may be a ring or a partial ring.

Figure 15:
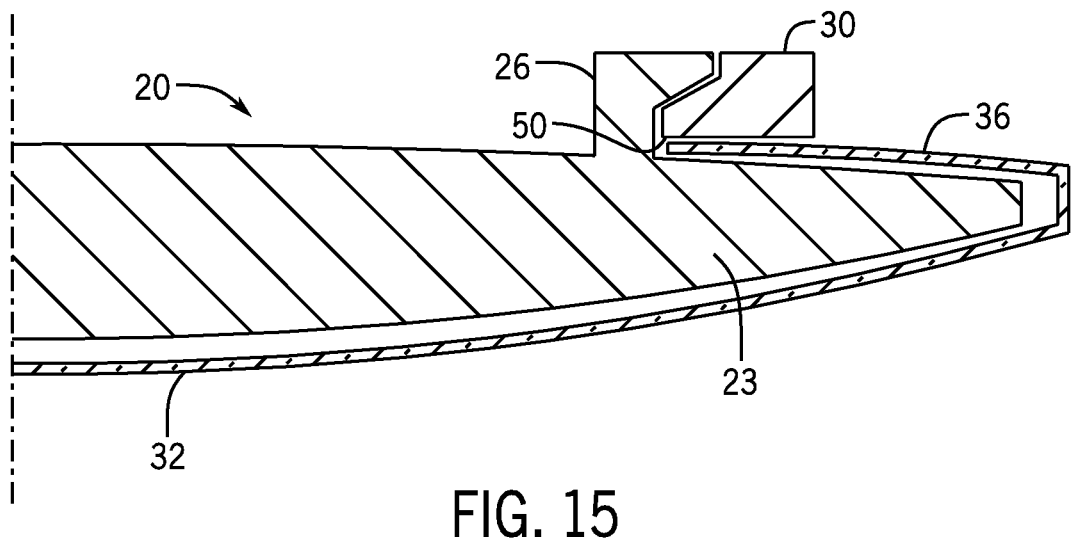
FIGS. 15-22 show various embodiments of the intraocular device in FIG. 14.

FIGS. 14 and 15 each show an embodiment in which the thickness of the secondary device 30 tapers toward the inner diameter 50 of the ring in a wedge shape, and the corresponding wedge shape of the supracapsular extensions 26 faces outward. The complementary wedge shapes of the secondary device 30 and the supracapsular extensions 26 provide a stable configuration of the primary intracapsular device 23 coupled to the secondary device 30 with the anterior capsule 36 sandwiched between the primary intracapsular device 23 and the secondary device 30.

Figure 16:
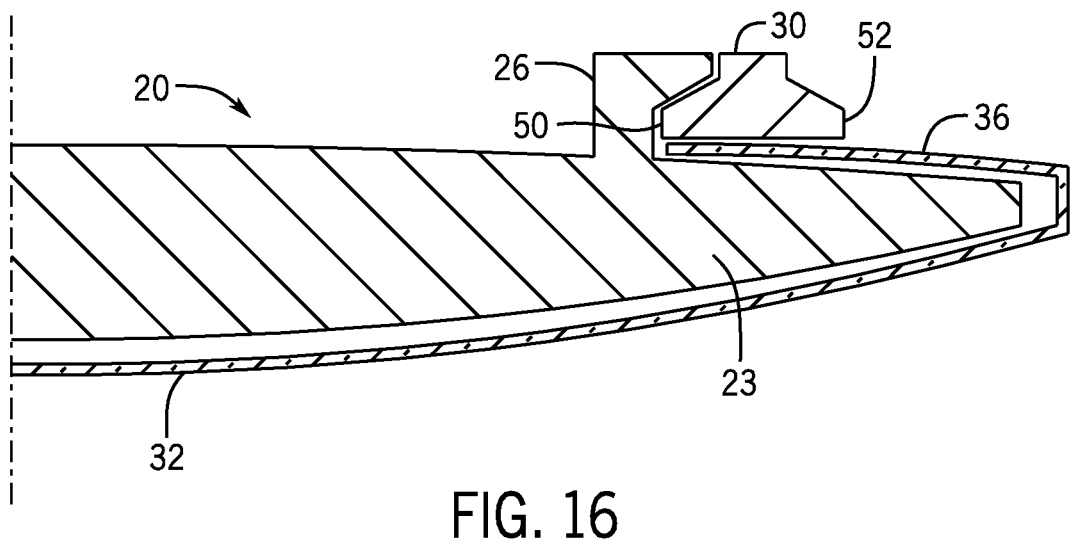

The intraocular device 20 in FIG. 16 is very similar to the embodiment shown in FIG. 15, but in FIG. 16 the secondary device 30 tapers toward the inner diameter 50 of the ring and also tapers toward the outer diameter 52 of the ring forming a wedge along each edge, with the thickness of the secondary device 30 being greatest between the inner diameter 50 and the outer diameter 52 of the ring.

Figure 17:
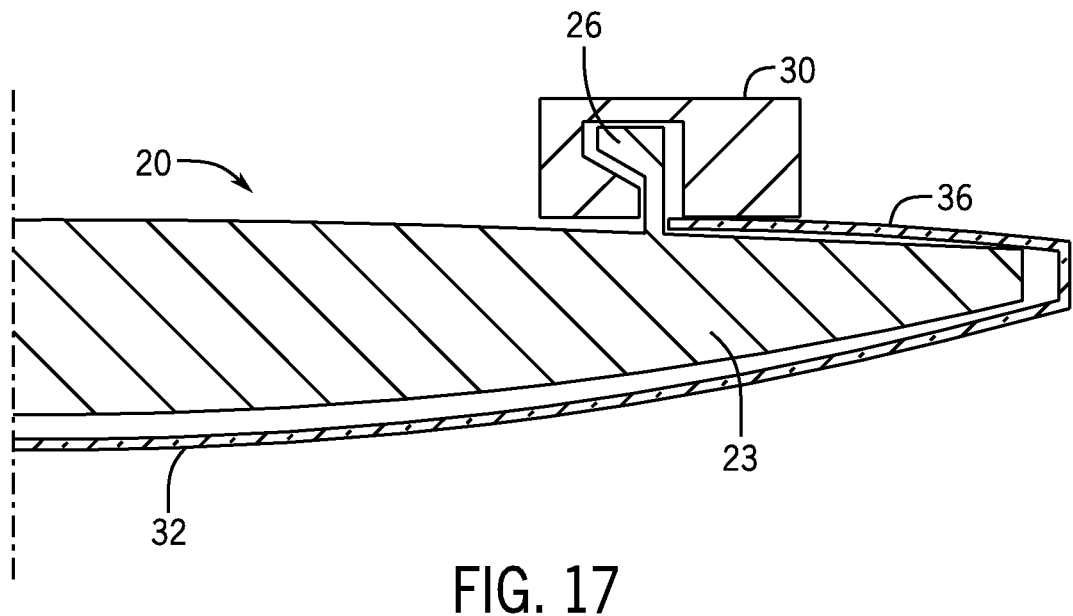

In FIG. 17, the secondary device 30 has a waveform surface configuration along a body of the ring. This waveform can interlock with the corresponding shape of the supracapsular extensions 26. This particular waveform is just one embodiment of a waveform. Other waveforms may be used. For example, the supracapsular extensions 26 in FIG. 17 have a wedge that faces inward and the waveform surface configuration of the secondary device 30 has a wedge portion that fits together with the wedge of the supracapsular extensions. Alternatively, the supracapsular extensions 26 may have a wedge that faces outward and the waveform surface configuration of the secondary device 30 may have a wedge portion that fits together with the wedge of the supracapsular extensions, in a configuration opposite of FIG. 17, for example.

Figure 18:
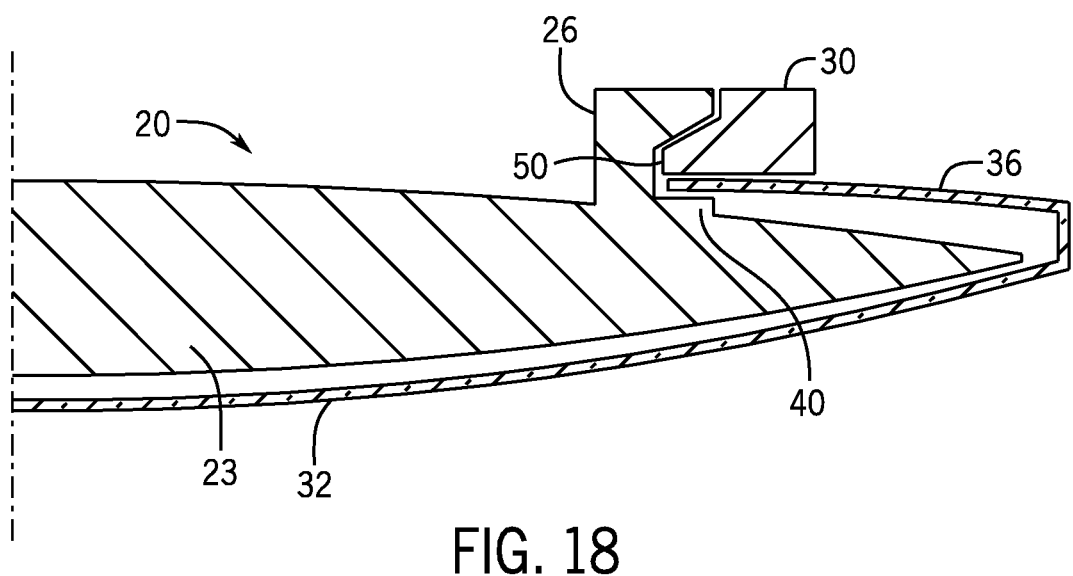

The intraocular device 20 in FIG. 18 is very similar to the embodiment shown in FIG. 15, but in FIG. 18 the primary intracapsular device 23 includes a step feature 40, similar to the step feature 40 shown in FIGS. 8 and 9. However, unlike the embodiment shown in FIG. 9, the step feature 40 in FIG. 18 is positioned within the capsular bag 32 beneath the anterior capsule 36. This step feature 40 may help secure the extensions 26 to the secondary device 30.

Figure 19:
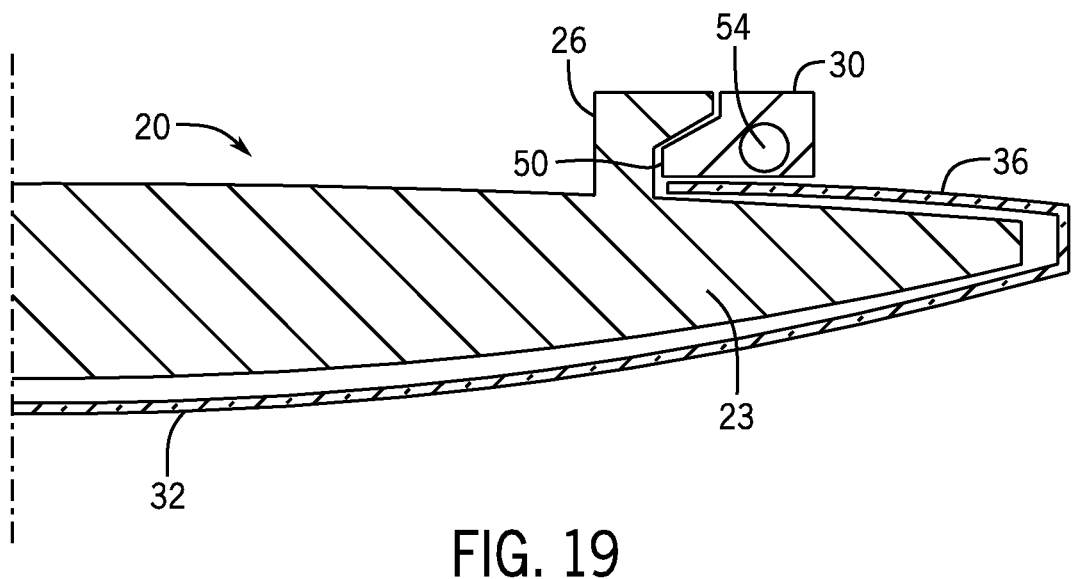

The intraocular device 20 in FIG. 19 is very similar to the embodiment shown in FIG. 15, but in FIG. 19 the secondary device 30 includes a nitinol or plastic ring 54 that can be used as a drug delivery device, described in greater detail below.

Figure 20:
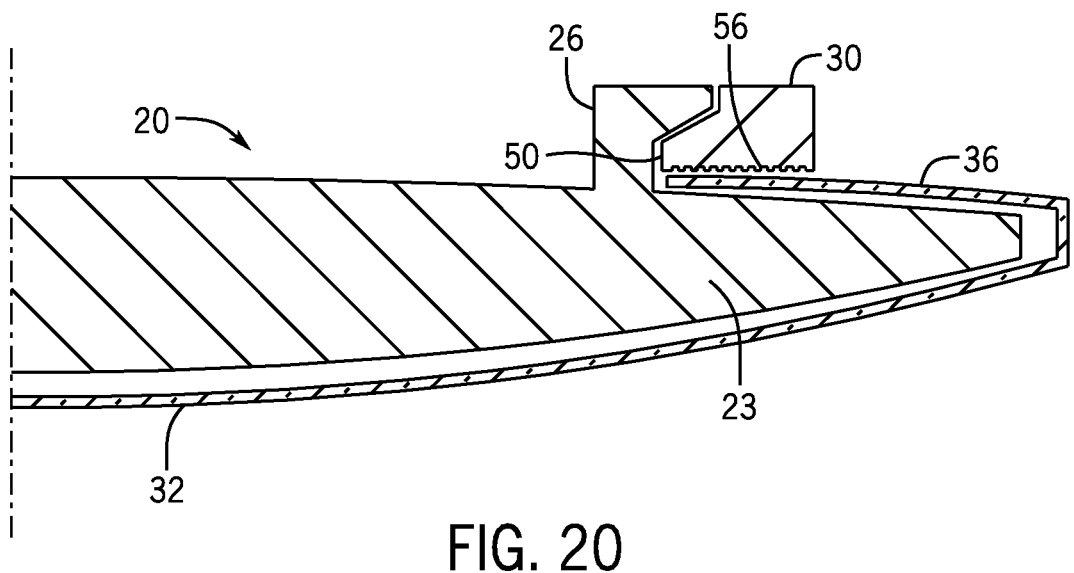

The intraocular device 20 in FIG. 20 is also very similar to the embodiment shown in FIG. 15, but in FIG. 20 the secondary device 30 includes a micro-pattern 56 on a bottom surface. The micro-pattern 56 may decrease the surface area available to contact the anterior capsule 36 while simultaneously helping to secure the secondary device 30 in place.

Figure 21:
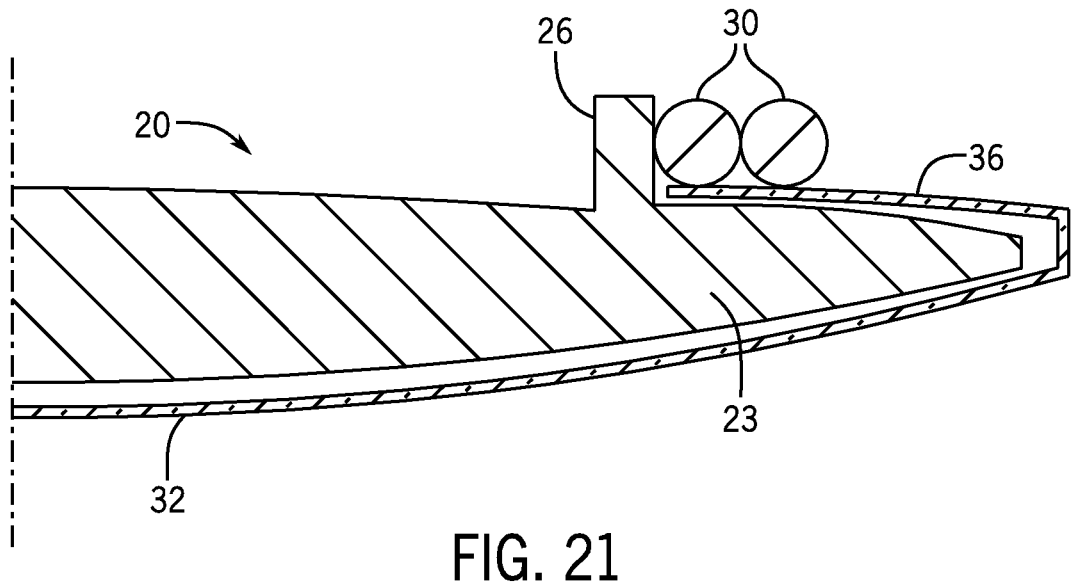
Figure 22:
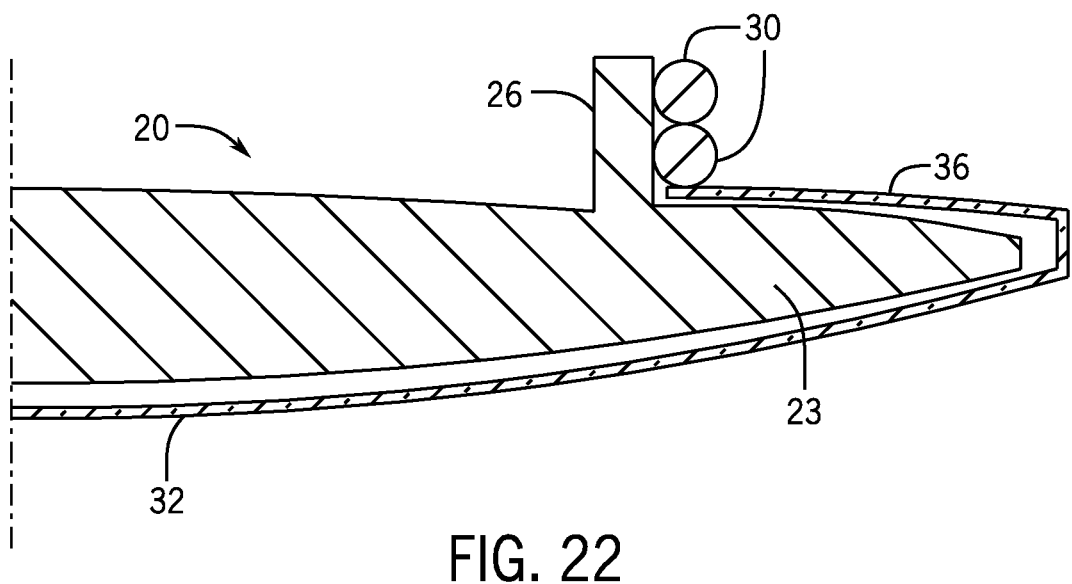

Multiple secondary devices 30 may be stacked either radially, as shown in FIG. 21, or vertically, as shown in FIG. 22, when the secondary devices 30 are connected to the supracapsular extensions 26. According to some embodiments, the first innermost or bottommost ring may touch the extensions 26 while the second and any subsequent rings may either be stacked abutting the first ring or may also connect directly to the extensions 26. This configuration allows for the delivery of different therapeutics using multiple rings as needed. In some embodiments, the rings may have gaps between them when stacked so that each ring is easily accessible with a surgical tool, such as a Sinskey hook, to remove each ring from the docked position without requiring excessive manipulation.

According to certain embodiments, the secondary device 30 may have a non-circular inner rim geometry and/or a non-circular outer rim geometry. An alternative inner rim geometry allows for positioning the ring over the extensions 26 without stretching the ring by aligning a maximum or larger inner diameter 50 of the ring over the extensions 26 and then rotating the ring relative to the extensions 26 until a shorter inner diameter 50 of the ring aligns with the extensions 26, which then fixes the ring in place by compression force. Likewise, an alternative outer rim geometry allows for positioning the ring between inward facing extensions 26 without compressing the ring by aligning a minimum or shorter outer diameter 52 of the ring between the extensions 26 and then rotating the ring relative to the extensions 26 until a larger diameter 50 of the ring aligns between the extensions 26, which then fixes the ring in place by compression force.

The secondary device 30 may be oval so that it locks into one or more tabs or other form of extensions 26 when rotated clockwise or counterclockwise after being positioned over the already-implanted intraocular lens 22. For example, the longer dimension of the oval ring may form wings that can be pulled up over the capsule and the shorter dimension of the oval ring may contain fenestrations that can be locked onto the extensions 26. This configuration facilitates injecting the intraocular device into the capsular bag followed by pulling the wings up over the anterior capsule with a Sinskey hook or similar device. Alternatively, the short dimension of the oval ring may be in the same axis as the haptics 28 so that the haptics 28 can open up and be visualized going into the capsular bag easily, as the ring does not obstruct the view of the haptics 28 opening up in the capsular bag.

Figure 23:
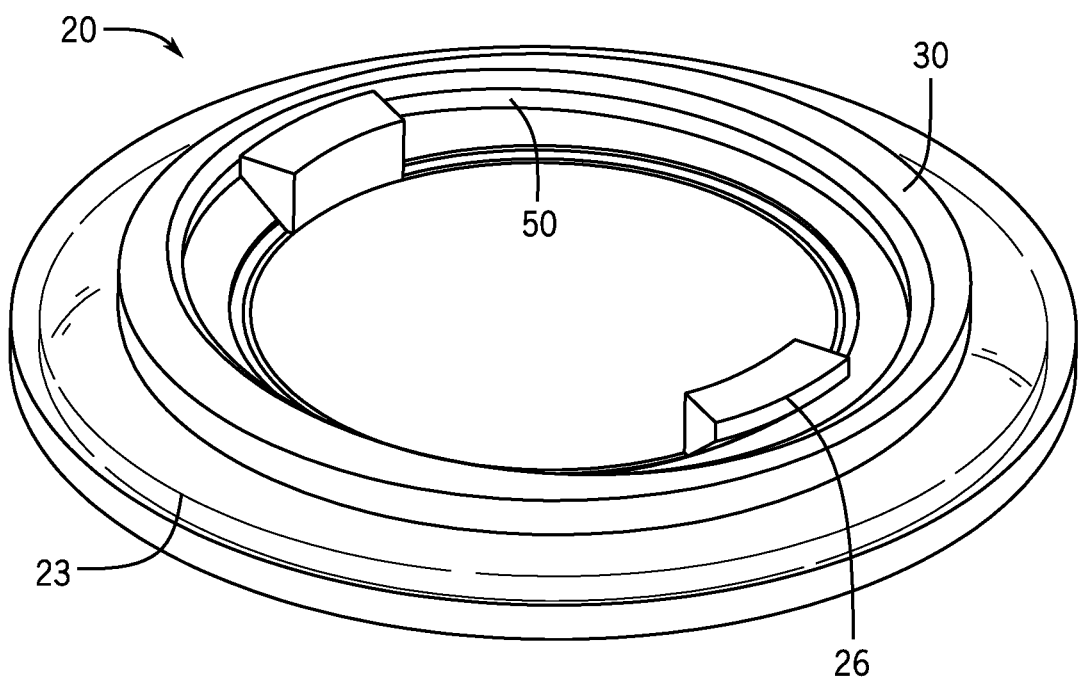
FIGS. 23-26 show perspective views of embodiments of the intraocular device having a non-circular inner rim geometry.
Figure 24:
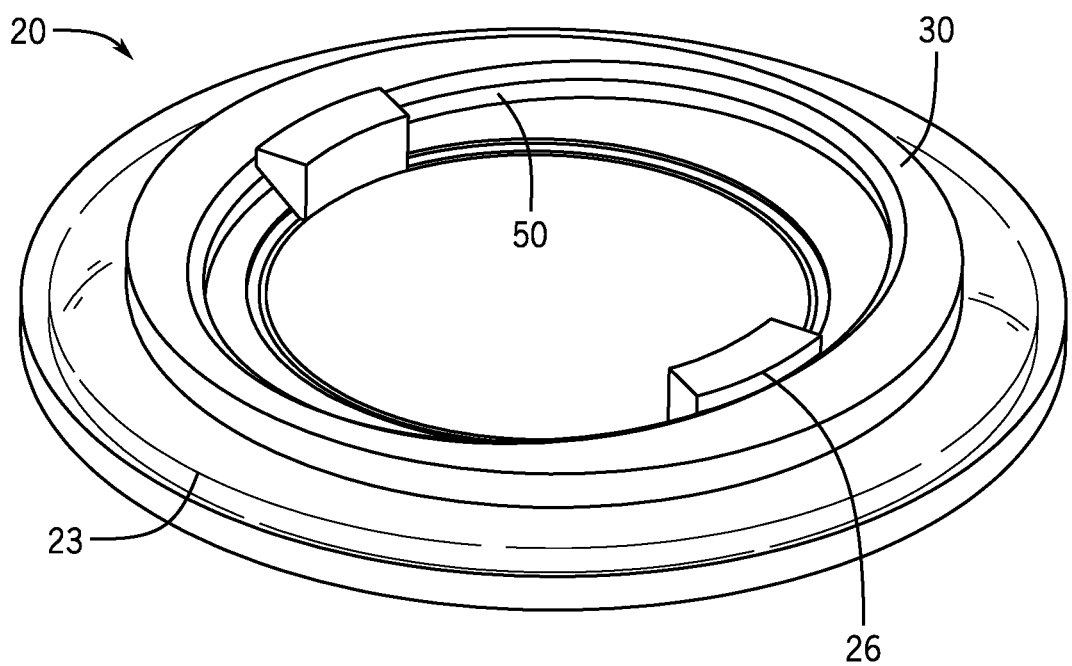

For example, as shown in FIGS. 23 and 24, the inner diameter 50 of the secondary device 30 may be oval in combination with outward facing extensions 26. In FIG. 23, the maximum inner diameter 50 of the oval ring is aligned with the extensions 26. In FIG. 24, the ring has been rotated such that a shorter inner diameter 50 of the ring aligns with and is held in place by the extensions 26. If the extensions 26 were inward facing and the outer diameter 52 of the secondary device 30 were oval, the minimum outer diameter 52 of the oval ring could be aligned between the extensions 26, and the ring subsequently rotated to align the larger outer diameter 52 between the extensions 26 in a stable and secure interlocking configuration.

Figure 25:
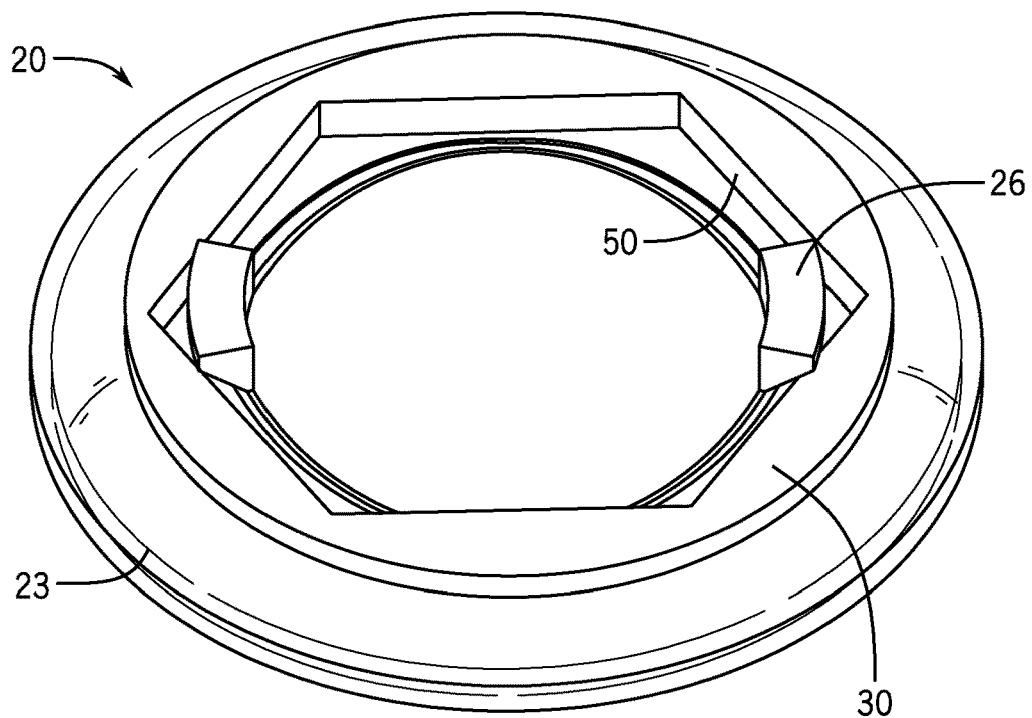
Figure 26:
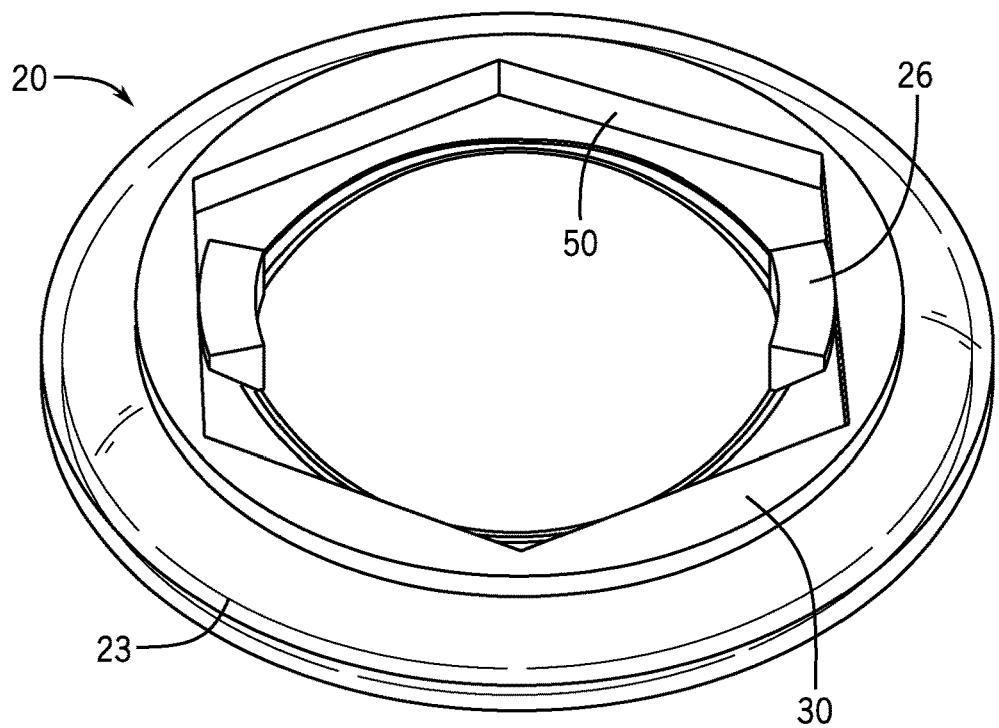

As another example, FIGS. 25 and 26 show the inner diameter 50 of the secondary device 30 having a hexagon shape in combination with outward facing extensions 26. In FIG. 25, a maximum inner diameter 50 of the hexagonal ring is aligned with the extensions 26. In FIG. 26, the ring has been rotated such that a shorter inner diameter 50 of the ring aligns with and is held in place by the extensions 26. As in the previous embodiments, if the extensions 26 were inward facing and the outer diameter 52 of the secondary device 30 were hexagonal, the minimum outer diameter 52 of the hexagonal ring could be aligned between the extensions 26, and the ring subsequently rotated to align the larger outer diameter 52 between the extensions 26 in a stable and secure interlocking configuration.

The intraocular device 20 may include one or more of the aforementioned features designed to secure the secondary device 30 and the extensions 26. For example, in the embodiments shown in FIGS. 23-26, the inner diameter 50 of the ring may include a micro-pattern to enhance fixation post rotation into place.

Rather than securing the secondary device 30 to the primary intracapsular device 23 with extensions 26, according to certain embodiments, the secondary device 30 can be coupled directly to the primary intracapsular device 23 by fit and/or by adhesive. In such embodiments, the primary intracapsular device 23 can be virtually any conventional intraocular lens 22 with the secondary device 30 formed separately and subsequently attached to the intraocular lens 22. In the embodiment shown in FIG. 27, the secondary device 30 is in the form of two partial rings or ring segments. Each of the ring segments may have a snap-fit or other mechanical fit onto the primary intracapsular device 23, or the ring segments may be secured to the primary intracapsular device 23 with an adhesive.

The secondary device 30 may be designed to hold a tertiary device 39 that can be implanted either at the time of initial surgery or any time postoperatively. The tertiary device 39 may be in the form of a ring or one or more partial rings, for example, and may include a sheath that houses one or more drug delivery devices and one or more drugs. Ideally, the intraocular device 20 is positioned to receive the tertiary device 39 without having to manipulate the primary intracapsular device 23 or the secondary intracapsular device 30.

As noted above, the secondary device 30 may be a drug delivery device. For example, the secondary device 30 in FIG. 27 can contain one or more drugs, such as within drug pads integrated into the secondary device 30, and can release the drug or drugs over time after the intraocular device 20 is fully implanted in the capsular bag. After the initial drug in the secondary device 30 is fully released, a new drug refill, in the form of a tertiary device 39, which may be in a ring form or other suitable form, can be implanted to fit in the concave sections of the two opposing parts of the secondary device 30. If the tertiary device 39 is a drug contained within a ring, as shown in FIG. 28, the tertiary device 39 can be held in place by elastic force within the concave sections of the secondary device 30. The tertiary device 39 may be a ring in a classic circle shape or the tertiary device 39 may be made in other shapes that can extend beyond an outer diameter of the optic in order to leverage some of the space where the secondary device 30 is not present.

The tertiary device 39 may be virtually any device affixed to the secondary device 30 to treat, diagnose, monitor or otherwise benefit ophthalmic or systemic diseases or conditions. When present, like the secondary device 30, the tertiary device 39 can perform optic functions, including refraction correction, presbyopia correction, such as providing extended depth of focus, and resolving dysphotopsia. For example, the tertiary device 39 may be a drug, a drug delivery device, an optical mask, a pinhole mask, a refractive mask, a toric mask, a multifocal mask, a trifocal mask, an opaque light-blocking surface, a partial light-blocking surface, and/or a dyspho ring. In certain cases, the tertiary device 39 may act as an artificial iris, such as in cases of trauma to the iris, or in cases of albinism or aniridia, for example. The tertiary device 39 may be any suitable form, such as a ring, a partial ring or ring segment, multiple ring segments, or a polygon.

Figure 28:
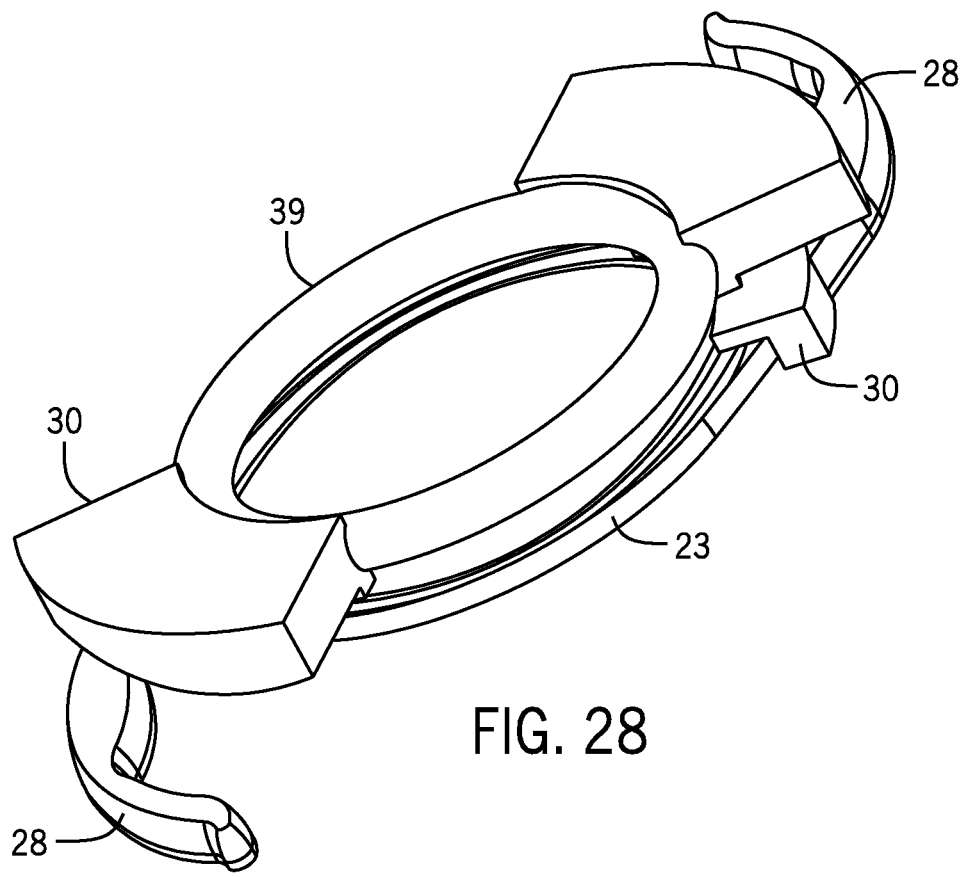
FIG. 28 is a perspective view of the intraocular device in FIG. 27 equipped with a tertiary device.
Figure 29:
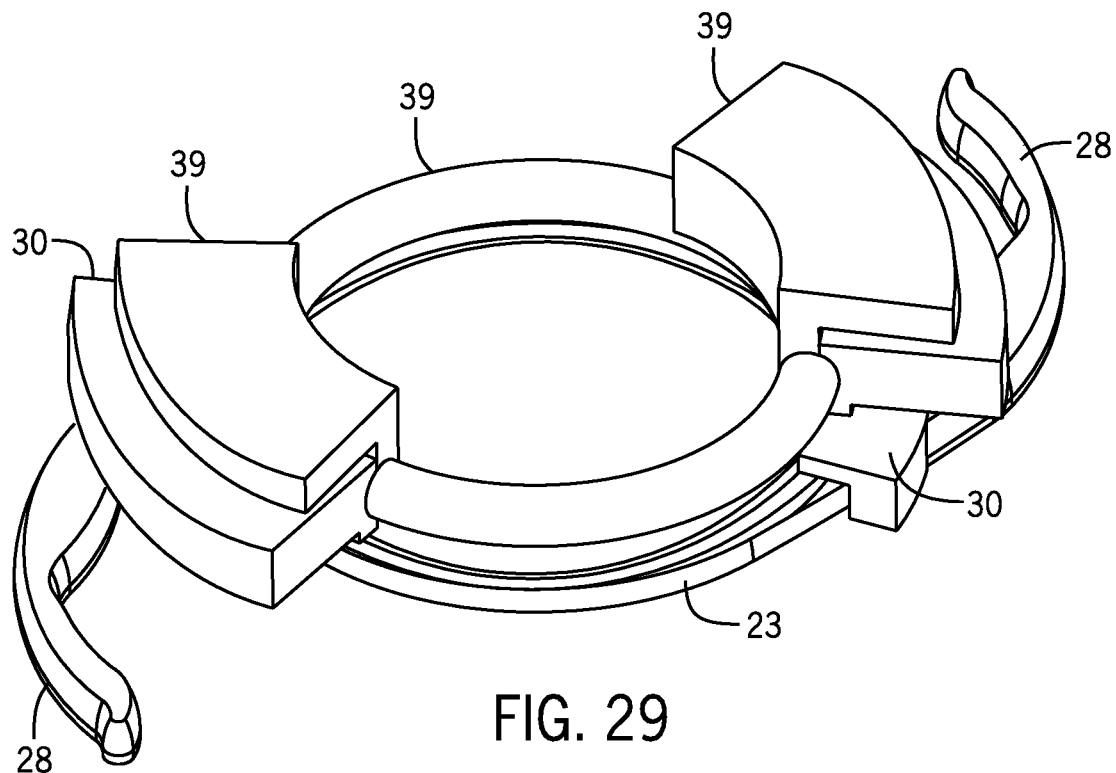
FIG. 29 is a perspective view of the intraocular device in FIG. 28 equipped with an additional tertiary device.

FIG. 29 shows the intraocular device 20 in FIG. 28 with a tertiary device 39 attached on top of the secondary device 30. In this particular embodiment, the tertiary device 39 is in the form of drug pads. The drug pads of the tertiary device 39 can be positioned over the ring segments of the secondary device 30, as shown. Alternatively, the tertiary device 39 can be positioned over part or all of the secondary device 30.

Figure 27:
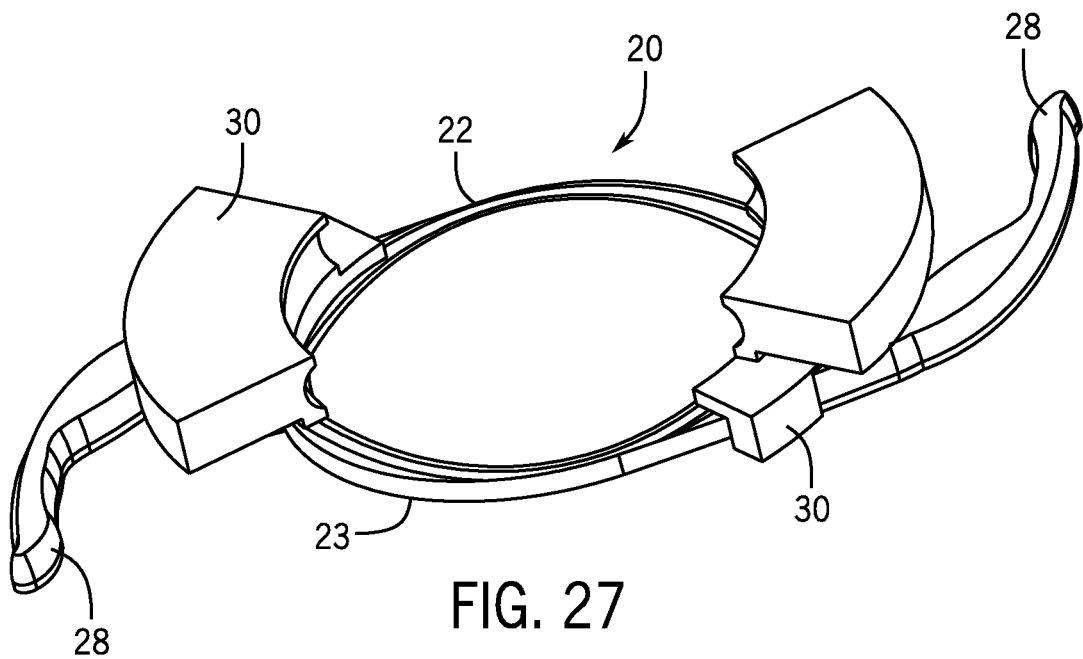
FIG. 27 is a perspective view of another embodiment of an intraocular device.

When the secondary device 30 is a secondary intracapsular device, as shown in FIGS. 27-29, the tertiary device 39 held in place by the secondary intracapsular device can either be positioned beneath an anterior capsule of the patient's eye within the capsular bag, or positioned outside the capsular bag with an anterior capsule of the patient's eye positioned between the tertiary device and the secondary intracapsular device, or positioned partially within the capsular bag and partially above an anterior capsule of the patient's eye.

Figure 30:
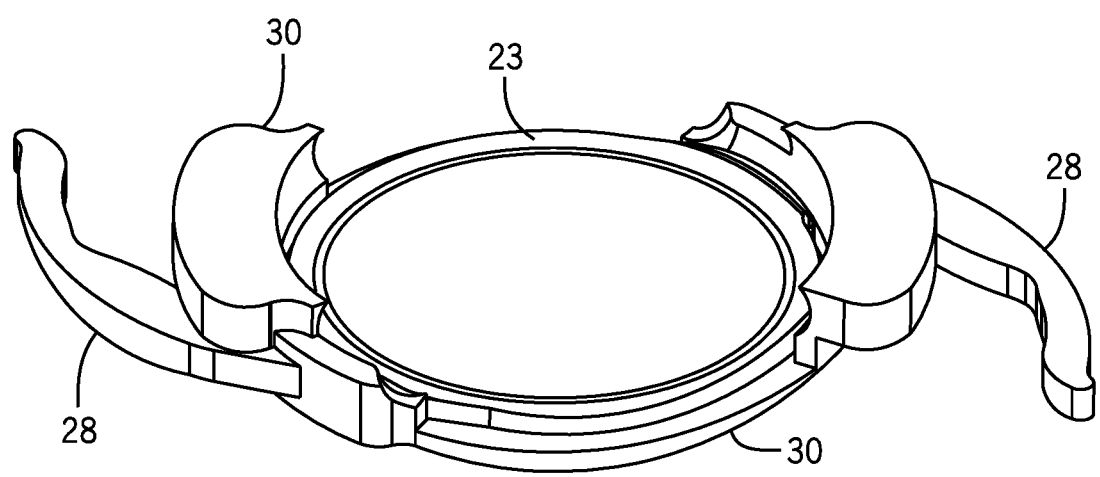
FIG. 30 is a perspective view of another embodiment of an intraocular device.
Figure 31:
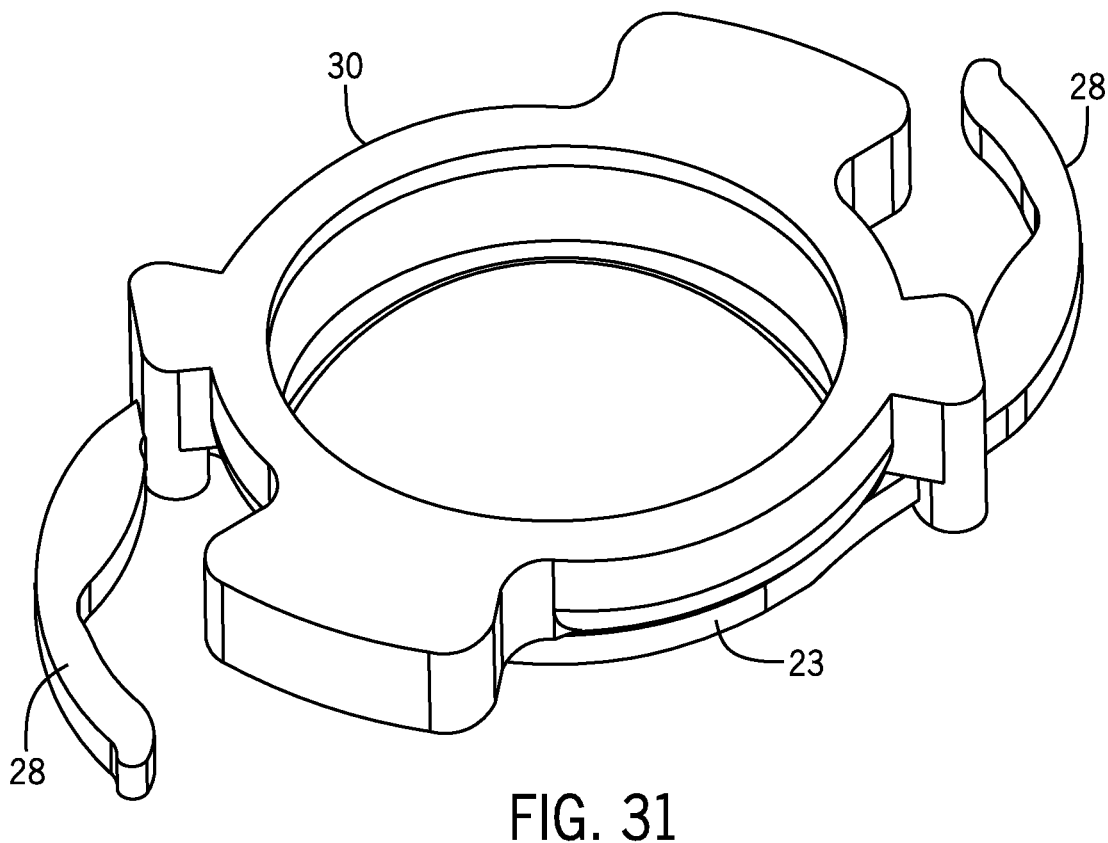
FIG. 31 is a perspective view of yet another embodiment of an intraocular device.

The secondary device 30 itself can extend both beneath and above the primary intracapsular device 23 as a way to join the secondary device 30 to the primary intracapsular device 23, as shown in FIG. 30. This sort of attachment can be used in the form of one or more ring segments, as shown in FIG. 30, as well as with a secondary device 30 in the form of a full ring. FIG. 31 shows another embodiment in which the secondary device 30 extends both beneath and above the primary intracapsular device 23, but in this embodiment the secondary device 30 is in the form of a full ring on the anterior side of the primary intracapsular device 23 with ring segments extending around the posterior side of the primary intracapsular device 23. According to certain embodiments, the primary intracapsular device 23 may be molded, lathed, printed or otherwise manufactured in one piece with the secondary device 30 and, optionally, with the tertiary device 39. For example, the primary intracapsular device 23 and the secondary intracapsular device 30 may be formed together in a single structure, or the primary intracapsular device 23 and the secondary extracapsular device 30 may be formed together in a single structure. Additionally or alternatively, the secondary device 30 may be coupled to the primary intracapsular device 23 by one or more extensions 26 or haptics 28 extending from the primary intracapsular device 23 through one or more holes in the secondary device 30.

Figure 32:
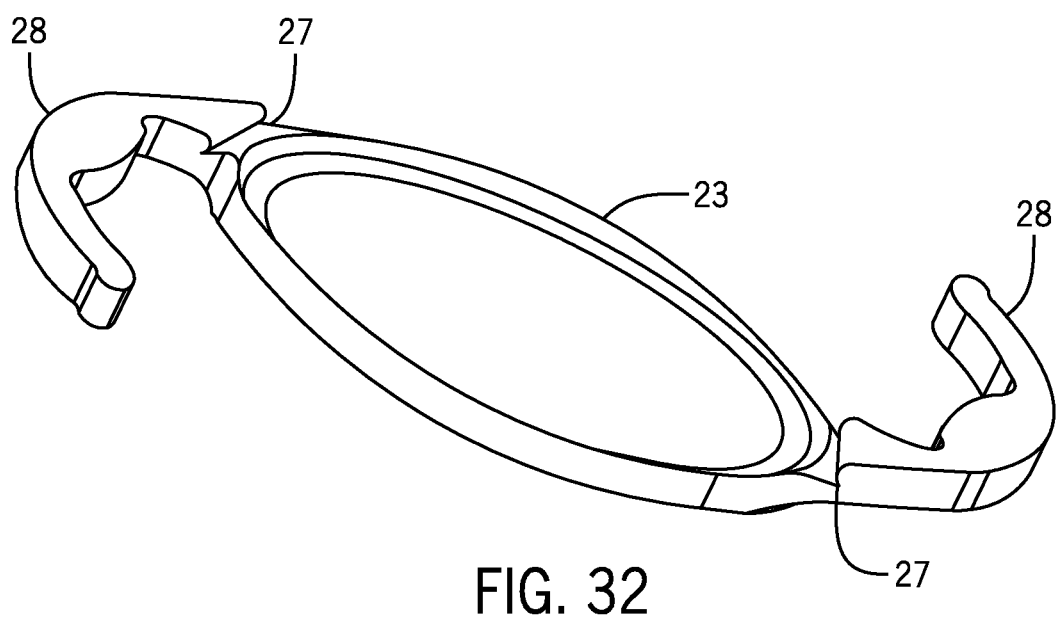
FIG. 32 is a perspective view of another embodiment of a primary intracapsular device.

FIG. 32 shows one embodiment of a primary intracapsular device 23 that can be joined to the secondary device 30. In FIG. 32, the intraocular device 20 includes a flare 27 in the optic haptic junction on each of the diametrically opposed sides of the primary intracapsular device 23 that act as the supracapsular extensions. Any of the described embodiments of the secondary device 30 can be held in place by the flares 27.

Figure 33:
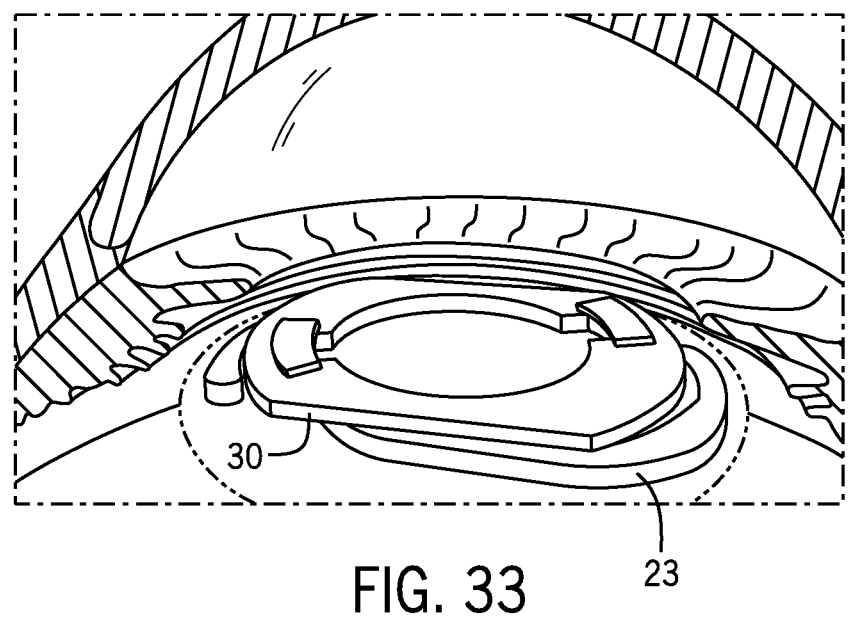
FIG. 33 is an implanted view of another embodiment of an intraocular device.
Figure 34:
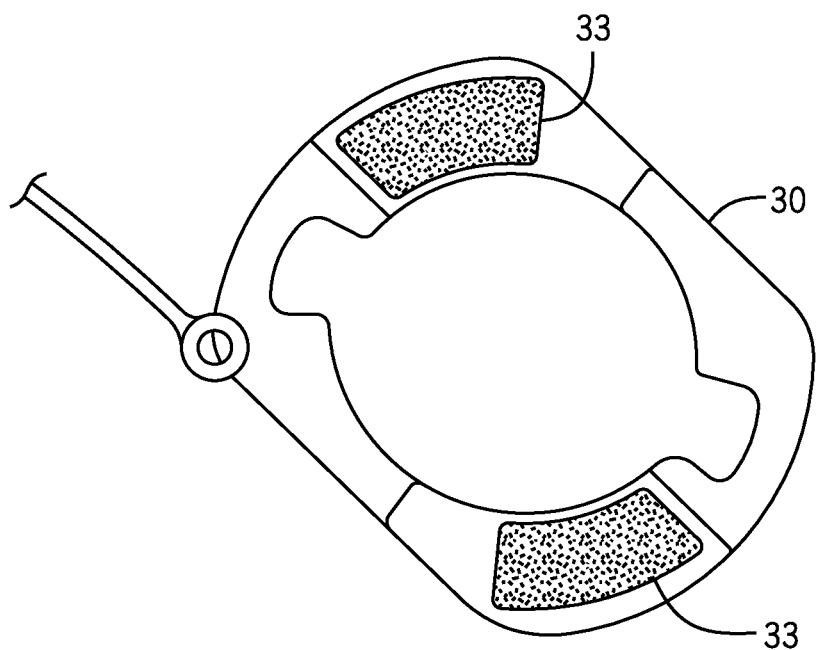
FIG. 34 is a plan view of a secondary device in FIG. 33.

FIG. 33 shows an embodiment of the secondary device 30 joined to the primary intracapsular device 23 implanted in a patient's eye. The secondary device 30 is shown in greater detail in FIG. 34. Pads 33 on the secondary device 30, as can be seen in FIG. 34, can be reinforced or more sturdy than a remainder of the secondary device 30, thereby providing suitable locations for locking into the extensions 26. For example, the pads 33 may be formed of a non-permeable material while a remainder of the secondary device 30 is permeable; however, the pads may contain some surface area that is permeable as well as non-permeable. The entire pad 33 may also be permeable. The degree of permeability is controlled by surface area, mix of permeable and non-permeable areas, as well as rate of permeability of the particular material that forms the outer structure of the pad 33.

Figure 35:
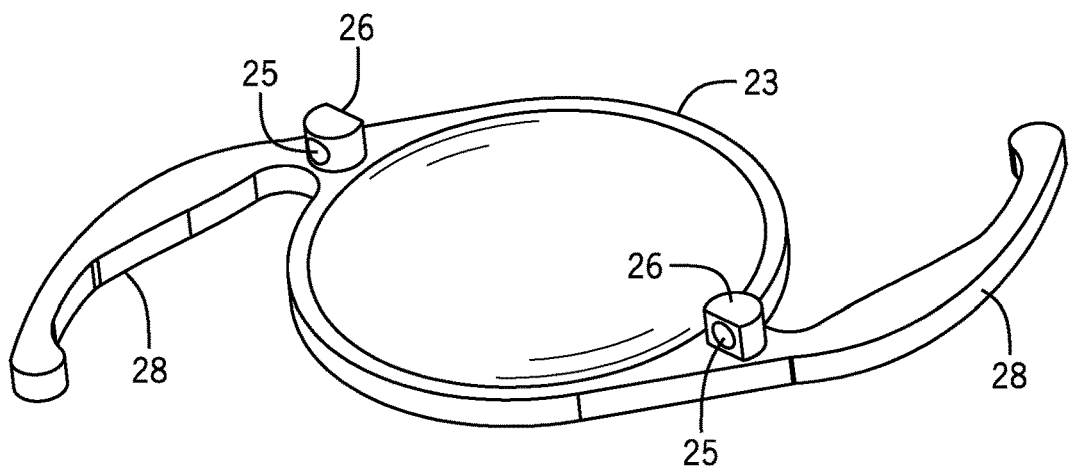
FIGS. 35 and 36 are plan views of one embodiment of interlocking parts of an intraocular device.
Figure 36:
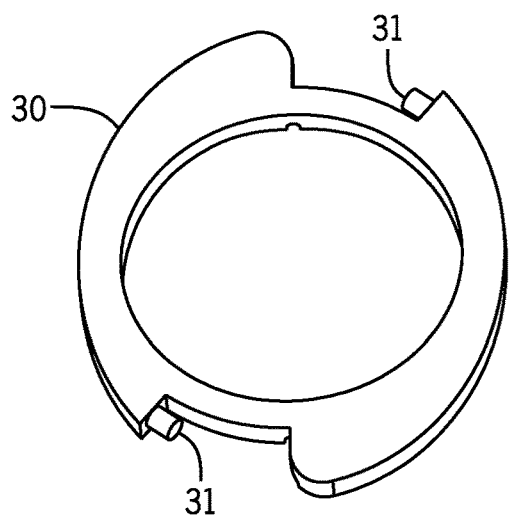

FIGS. 35 and 36 together show another embodiment for joining the secondary device 30 to the primary intracapsular device 23. In FIG. 35, the primary intracapsular device 23 includes extensions 26 each having a hole 25. In FIG. 36, the secondary device 30 includes protrusions 31. The secondary device 30 can be joined to the primary intracapsular device 23 by aligning the ring of the secondary device 30 atop the primary intracapsular device 23 and rotating the ring counterclockwise to fit the protrusions 31 into the corresponding holes 25 for enhanced attachment. This embodiment may be altered to adapt to a clockwise rotation as well. This embodiment may also be modified with the holes provided in the secondary device 30 and corresponding protrusions 31 extending from the extensions 26.

Figure 37:
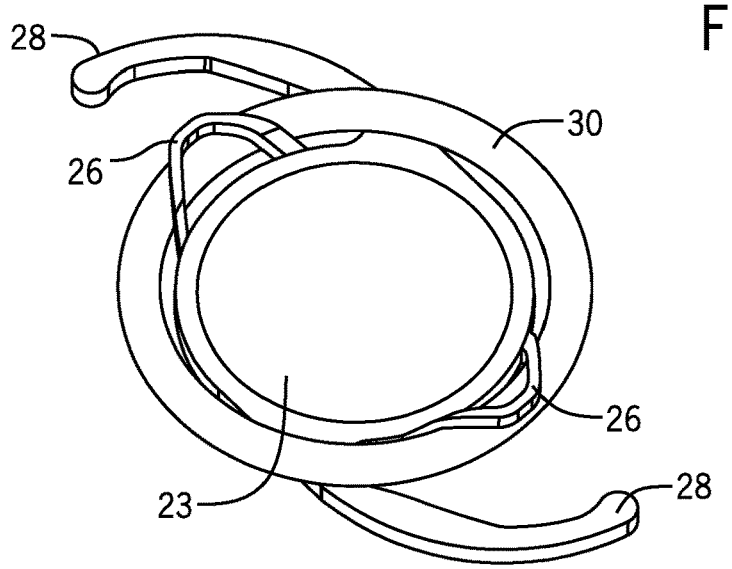
FIG. 37 is a plan view of another embodiment of an intraocular device.

The primary intracapsular device 23 in FIG. 35 can also be used in combination with a ring-shaped secondary device 30. More particularly, the ring can be affixed to the extensions 26 through the holes 25, provided the holes 25 extend fully through each extension 26, so that the ring makes a full circle that is connected by glue or other adhesive and is not detachable from the supracapsular extensions 26 without cutting the ring in one or more areas. Similarly, as shown in FIG. 37, the ring can be held in place beneath the extensions 26. Alternatively, the ring could be fed through the loops of the extensions 26 in FIG. 37, just as the ring could be fed through the holes 25 in the extensions 26 in FIG. 35. In order to feed the ring through the loops or holes, the ring would need to be opened or cut for assembly, and then the ends would need to be reattached by adhesive or hooks or interference fit or any other suitable form of re-connecting the ends of the ring to one another.

The secondary device 30 can also be joined to the primary intracapsular device 23 using magnetic forces. For example, one or more magnets can be provided in the extensions 26, which can be aligned with a corresponding magnet or magnets in the secondary device 30. The magnetic force can lock the secondary device 30 into place on the primary intracapsular device 23.

As noted, the secondary device 30, and in some cases the tertiary device 39, may serve as a drug delivery device for holding and releasing active pharmaceutical ingredients to treat the eye, such as beta blockers, alpha agonists, prostaglandin analogs, pilocarpine, rock-inhibitors, ethacrynic acid, CNP/BNP/ANP, carbonic anhydrase inhibitor, steroids, NSAIDs, antibiotics, biologic therapeutics, tetrahydrocannabinol (THC), cannabidiol (CBD), cannabinoids or other molecules derived from the *cannabis* plant, small or large molecule active ingredients, anti-fibrotic, miotic, mydriatic, anti-neoplastic, 11-epi-PGF$_{2\alpha}$, and/or other active ingredients that can treat ocular disease. For example, the secondary device 30 may provide long-term drug delivery, such as for treating glaucoma or macular degeneration, or short-term delivery of steroids, NSAIDS, or antibiotics following intraocular surgery. The secondary device 30 and tertiary device 39 may also be used to deliver biologic/non-biologic molecules for the treatment of any disease or disorder. The secondary device 30 and tertiary device 39 may contain more than one drug if a patient requires more than one type of therapy.

Figure 38:
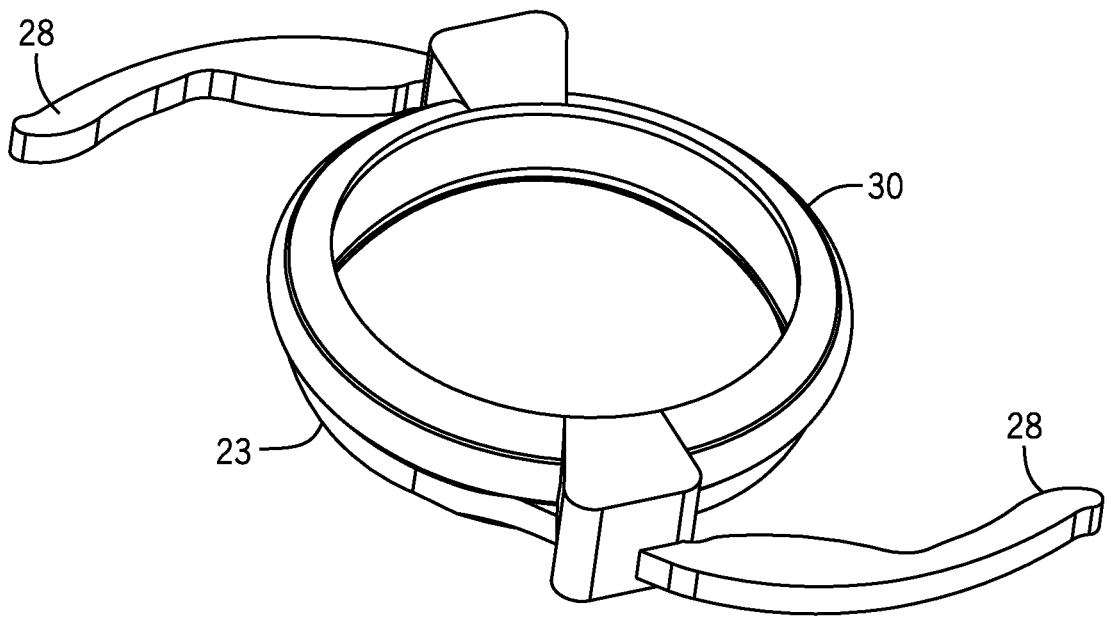
FIG. 38 is a perspective view of another embodiment of an intraocular device.
Figure 39:
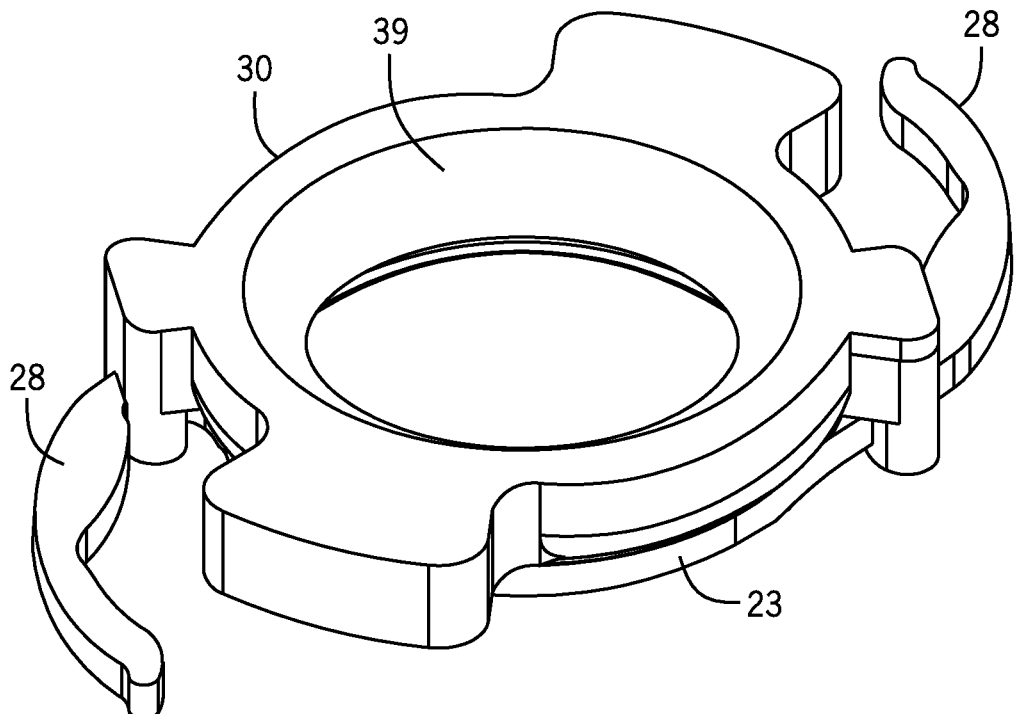
FIG. 39 is a perspective view of still another embodiment of an intraocular device.

According to some embodiments, the secondary device 30 may include a sheath in which a tertiary device 39 in the form of a drug delivery device may be contained, as shown in FIGS. 38 and 39. FIG. 38 shows the sheath, and FIG. 39 shows a drug delivery device contained in the sheath. In particular, the drug delivery device that is embedded in a silicone outer shell of the secondary device 30 may be designed so that the modulus of the drug delivery sheath causes enhanced compression or attachment against a supracapsular or intracapsular extension off of the primary intracapsular device 23 for greater lens stability. After an initial drug housed in the sheath is gone, a new drug delivery device can be implanted in the sheath. Furthermore, the sheath can contain a drug delivery device that can house a plurality of drugs. Optionally, the sheath can contain a plurality of drug delivery devices.

In some embodiments, the ring sheath may have surface areas that are not permeable to water or drugs so that a greater surface area can be used to enhance attachment of the sheath to the extensions but without greater surface area to elute.

According to certain embodiments, the secondary device 30 may include a refillable reservoir. The reservoir can be refilled with a fluid or solid. For example, the reservoir may be refilled every 6-12 months after the drug therein diffuses through the walls of the reservoir, such as by either Fickian or non-Fickian diffusion or through micro-holes or through a "sweating balloon" mechanism or any other suitable method for eluting the drug. As another example, the reservoir may receive a solid pellet, such as a sustained-release biodegradable implant, and hold the pellet in place while the pellet degrades. In this case, the reservoir need not be flow limiting. The entire reservoir may be made from a nitinol mesh or prolene suture material, which would allow for depositing of a pellet and keeping the pellet in place during eluting. Holding the pellet in place would prevent the pellet from harming intraocular tissues such as the back surface of the cornea.

Figure 40:
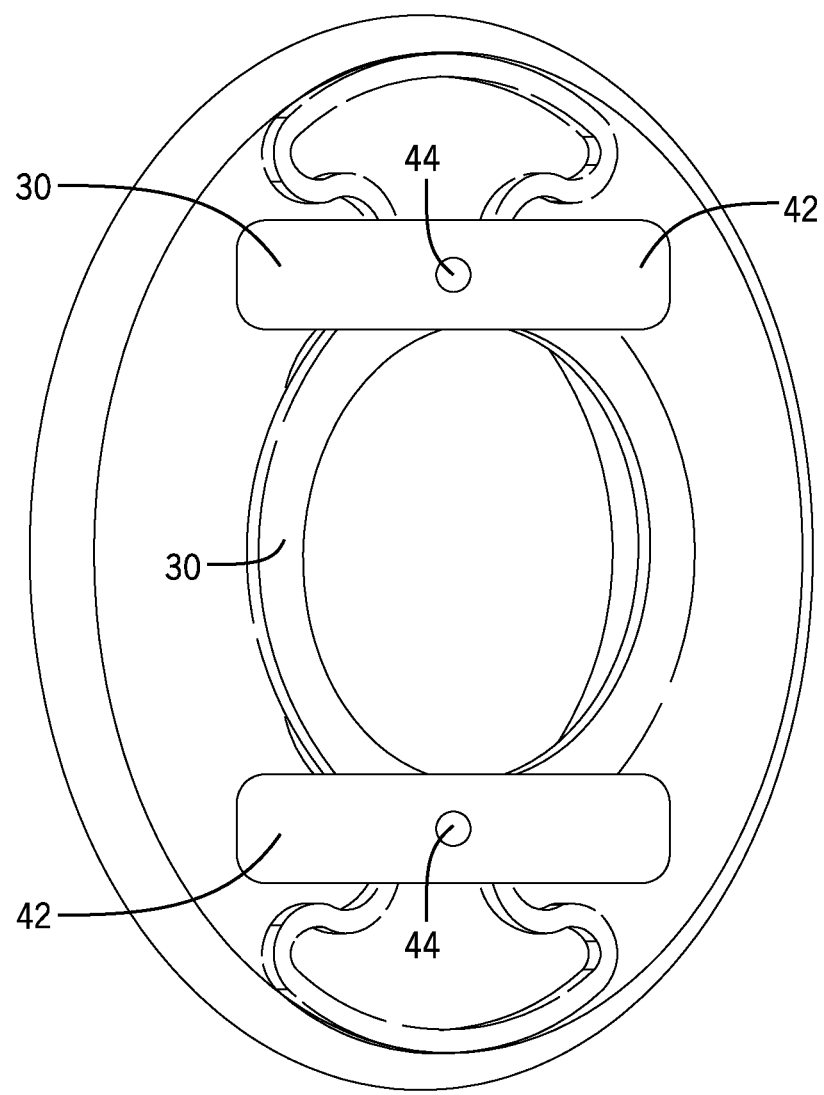
FIG. 40 is a perspective view of another embodiment of an intraocular device.

FIG. 40 shows a secondary device 30 in the form of a refillable reservoir. More particularly, the secondary device 30 includes a drug delivery bleb reservoir 42. The reservoir 42 may include a docking port 44 in order to refill the reservoir 42. The reservoir 42 may be formed of a polymer or other suitable materials. The docking port 44 is the entry point to refill the reservoir 42 with either a fluid or a solid. The docking port 44 may be a one-way valve or a swing door, depending on the drug and its intended release. For example, the docking port 44 can be akin to a Hickman catheter port. The ring portion of the secondary device 30 may or may not be included in combination with the drug delivery bleb reservoir 42.

Figure 41:
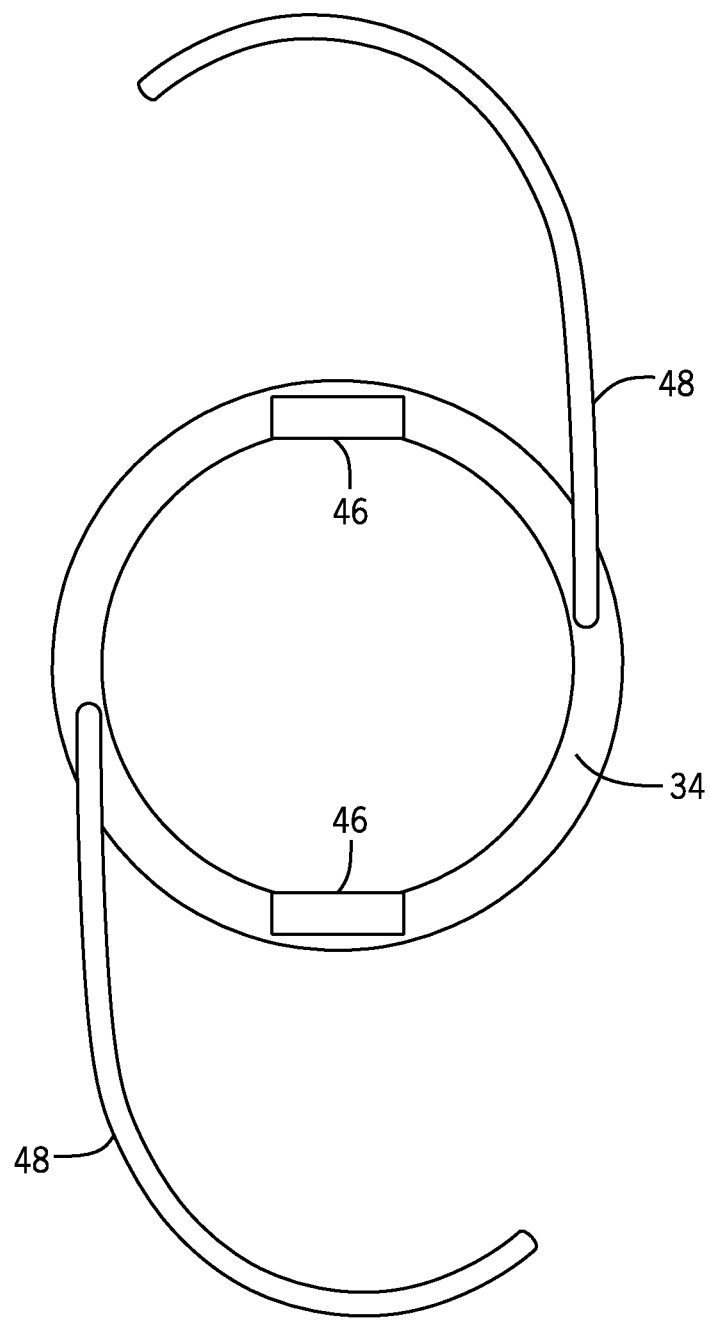
FIG. 41 is a plan view of an intraocular scaffold.

Another embodiment of the primary device in the form of an intraocular scaffold 34 is shown in FIG. 41. In this embodiment, the intraocular scaffold 34 resides entirely in the supracapsular space. More particularly, the scaffold 34 is implanted over the anterior capsule 36 and then the secondary device 30 attaches to one or more support features 46, which may be in the form of tabs, hooks, pegs, rings, a planar surface with indentations, pins, polygons, or other configurations adapted to receive the secondary device 30. One or more stabilizing features 48 that provide stability in the sulcus may be in the form of haptics, as shown in FIG. 41, or in the form of any other suitable attachment features that couple with surrounding tissues other than the sulcus. In one form, the device shown in FIG. 41 may attach to the anterior capsule 36 using clips with some portion of the clips extending both above and below the anterior capsule 36.

Figure 42:
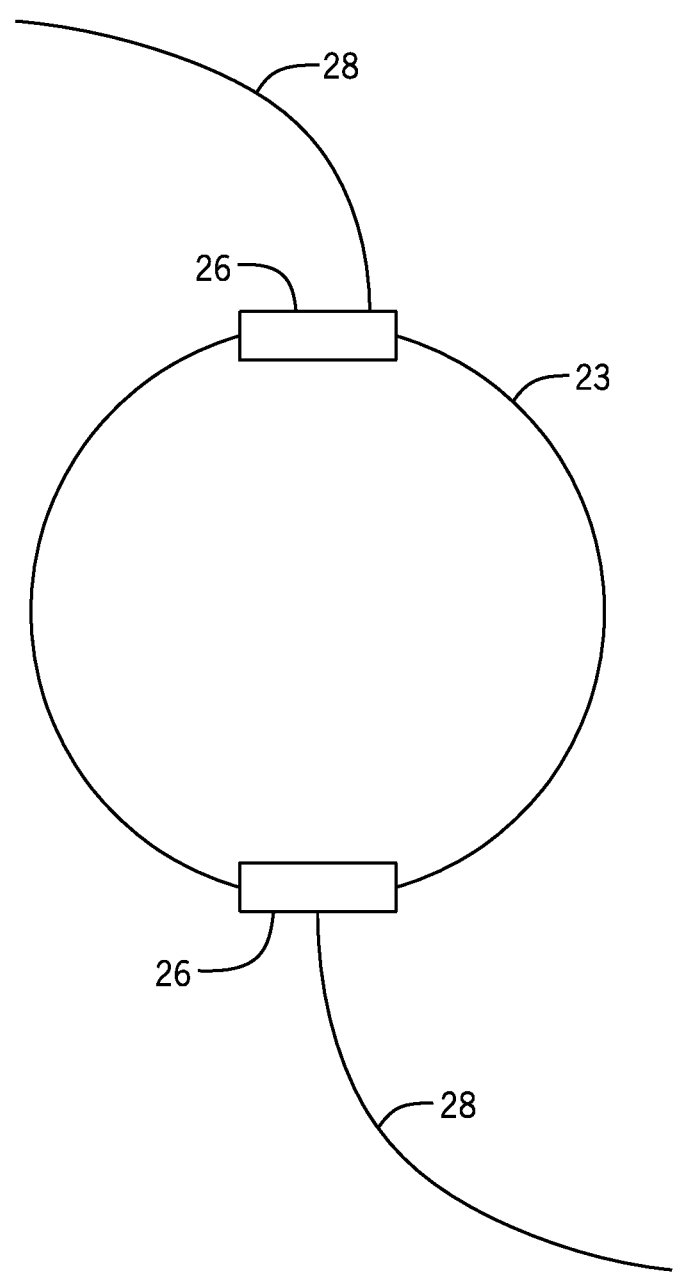
FIG. 42 is a plan view of another embodiment of an intraocular device.
Figure 43:
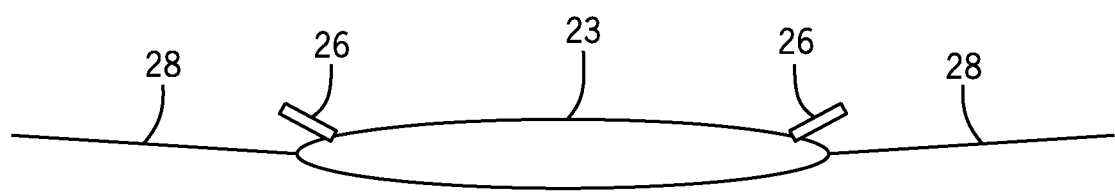
FIG. 43 is a side plan view of the intraocular device in FIG. 42.

Methods of implanting and using the intraocular devices 20 described herein can be performed using currently known surgical steps. According to one embodiment, a primary intracapsular device 23, such as the device shown in FIGS. 42 and 43, can be injected into a patient's eye. The primary intracapsular device 23 can be held in place and stabilized with haptics 28 extending from the primary intracapsular device 23 or any other suitable device for securing the primary intracapsular device 23 within the capsular bag. The secondary device 30 can then be implanted in the patient's eye and attached to the primary intracapsular device 23, such as with extensions 26 extending from an anterior side of the primary intracapsular device 23. Alternatively, the secondary device 30 may include retention features that can cross the anterior capsule plane into the capsular bag and attach to the already-implanted primary intracapsular device 23, which itself has complementary attachment features. The joined secondary device and primary intracapsular device 23 can then be positioned within the patient's eye with the extensions 26 terminating above a position of the anterior capsule 36 of the lens bag 32 in the patient's eye as supracapsular extensions 26, and the primary intracapsular device 23 held in place by the capsular bag of the patient's eye and the secondary device held in place by the primary intracapsular device 23.

According to another embodiment, the secondary device 30 can be attached to the primary intracapsular device 23, such as with extensions 26. The joined secondary device 30 and primary intracapsular device 23 can then be injected into a patient's eye with the primary intracapsular device 23 held in place by the capsular bag of the patient's eye and the secondary device 30 held in place above the anterior capsule 36 by the primary intracapsular device 23. According to certain embodiments, the secondary device 30 may be positioned between the anterior capsule 36 and an iris without the secondary device 30 touching either the anterior capsule 36 or the iris. Alternatively, the joined secondary device 30 and primary intracapsular device 23 can be injected into a patient's eye with both the primary intracapsular device 23 and the secondary device 30 positioned fully inside in the patient's capsular bag.

Figure 44:
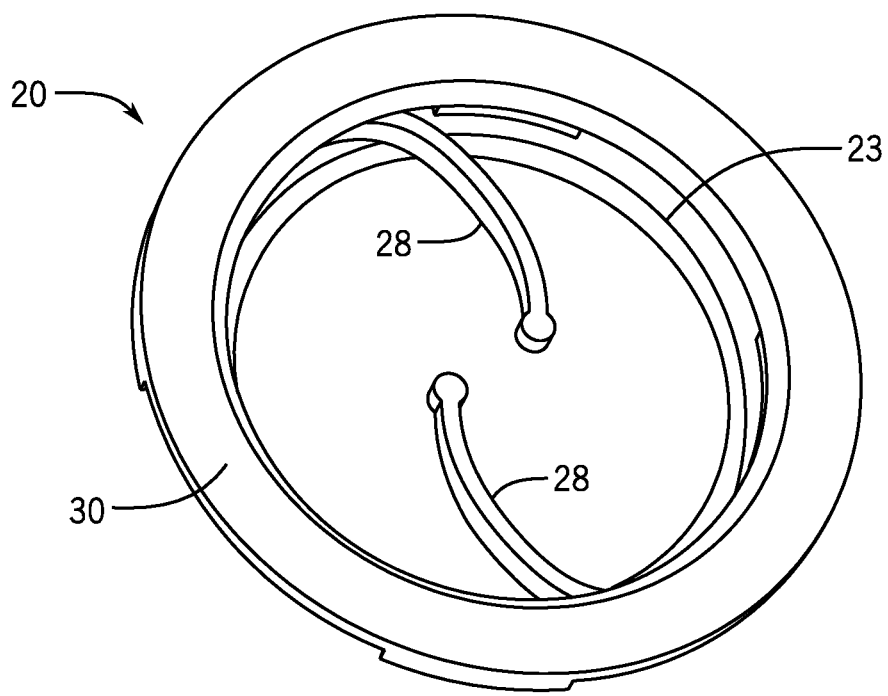
FIG. 44 is a perspective view of yet another embodiment of an intraocular device.
Figure 45:
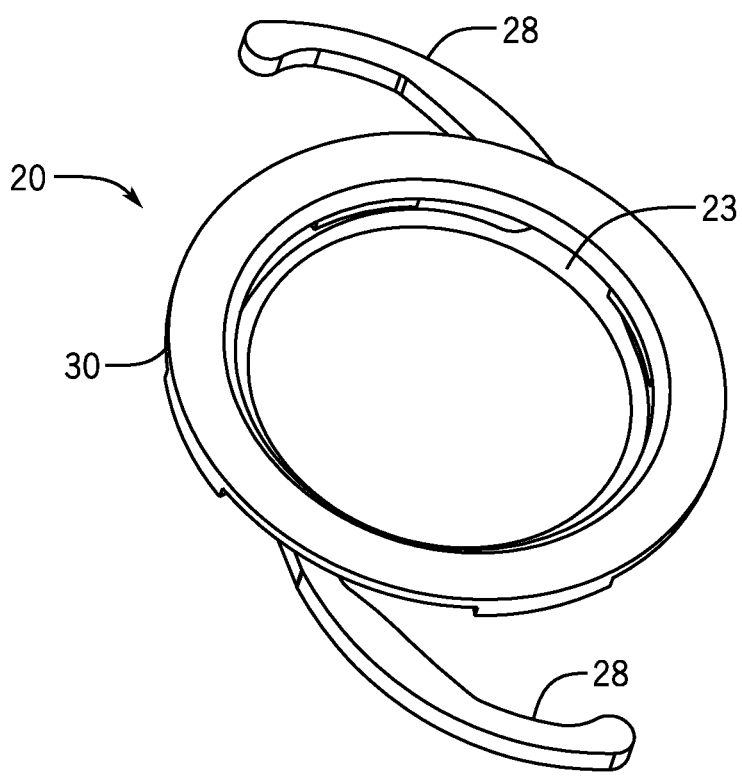
FIG. 45 is another perspective view of the intraocular device in FIG. 44.

As shown in FIG. 44, the haptics 28 from the primary intracapsular device 23 can be placed within a gap between the primary intracapsular device 23 and the secondary device 30 to be injected as one assembly. When injected in the patient's eye, the secondary device 30 is supported by the anterior capsule followed by displacing the haptics 28 manually, by the surgeon, so that the haptics 28 slide out of the slots and open up in the capsular bag, as shown in FIG. 45. The gap or gaps between the primary intracapsular device 23 and the secondary device 30 may be formed from undulations or micro-patterns in a bottom surface of the secondary device 30 facing the primary intracapsular device 23.

A tertiary device 39 can be attached to the secondary device 30 either before or after the intraocular device 20 is implanted in the patient's eye. Since the tertiary device 39 can be easily attached to the secondary device 30, when the intraocular device 20 has already been implanted, the tertiary device 39 can be attached to the secondary device 30 without having to manipulate the primary intracapsular device 23 or the secondary device 30.

The implantation of the intraocular devices 20 can be performed during or after intraocular surgery, such as cataract surgery. More particularly, after removing the cataract lens, the primary intracapsular device 23 can be implanted, such as with haptics, and the extensions 26 can extend from the primary intracapsular device 23 through the opening from which the cataract was removed.

As explained above, the secondary device 30 can be used to treat, diagnose, or monitor ophthalmic or systemic diseases or conditions. For example, the secondary device 30 can be used for long-term drug delivery, short-term drug deliver, and/or the delivery of biologic or non-biologic molecules to the eye. In certain embodiments, the secondary device may include a refillable reservoir, which may be filled with a fluid or a solid. Additionally, the secondary device 30 can be used as an artificial iris. When necessary or beneficial, the secondary device 30 may be removed. Also, when necessary or beneficial, after removal the secondary device 30 may be replaced with either the same type of secondary device 30 or another secondary device 30 that may be deemed more beneficial under the circumstances. Likewise, a tertiary device 39 can be used to treat, diagnose, or monitor ophthalmic or systemic diseases or conditions.

Benefits of the intraocular devices 20 described herein include the ability to treat, diagnose, monitor or otherwise benefit ophthalmic or systemic diseases or conditions with minimal residual discomfort in the patient's eye, as well as providing substantial lens stability.

The descriptions and figures included herein depict specific implementations to teach those skilled in the art how to make and use the best option. For the purpose of teaching inventive principles, some conventional aspects have been simplified or omitted. Those skilled in the art will appreciate variations from these implementations that fall within the scope of the invention. Those skilled in the art will also appreciate that the features described above can be combined in various ways to form multiple implementations. As a result, the invention is not limited to the specific implementations described above, but only by the claims and their equivalents.

What is claimed is:

1. An ophthalmic implant comprising:
   a multi-part IOL assembly comprising a primary device (23) comprising an IOL (22) and a secondary device comprising a first drug delivery device (30);
   wherein:
   said IOL (22) comprising a lens (24), a tab (26), and a haptic (28);
   said tab (26) extending from the IOL (22), and said tab (26) configured to engage the first drug delivery device (30);
   said haptic (28) extending radially outwardly from the lens (24), such that said haptic (28) is configured to hold the IOL (22) in place within a capsular bag of a patient's eye;
   said first drug delivery device (30) comprises a ring configured for a mechanical fit on the tab (26); and
   in an assembled configuration, the first drug delivery device (30) is engaged in said mechanical fit with the tab (26) to secure the first drug delivery device (30) to the IOL (22) such that the tab (26) extends from the IOL (22) through a hole in the first drug delivery device (30) to establish said mechanical fit on the tab (26).

2. The ophthalmic implant of claim 1, wherein:
   the first drug delivery device (30) comprises a drug pad integrated into the first drug delivery device (30).

3. The ophthalmic implant of claim 1, wherein:
   the first drug delivery device (30) is further configured to comprise a drug pad.

4. The ophthalmic implant of claim 1, wherein:
   the first drug delivery device (30) further comprises a refillable reservoir.

5. The ophthalmic implant of claim 1, further comprising:
   a second drug delivery device (39) configured for attachment to the first drug delivery device (30).

6. The ophthalmic implant of claim 1, wherein:
   the haptic (28) extending radially outwardly from the lens (24) extends outwardly in a plane of the lens.

7. The ophthalmic implant of claim 1, wherein:
   the IOL (22) has an anterior side (24) and is configured for placement into the eye of a patient with said anterior side (24) disposed anteriorly in the eye of the patient; and
   the tab (26) extends from the anterior side (24) of the IOL (22).

* * * * *

UNITED STATES PATENT AND TRADEMARK OFFICE
CERTIFICATE OF CORRECTION

| | |
|---|---|
| PATENT NO. | : 11,298,262 B2 |
| APPLICATION NO. | : 16/516356 |
| DATED | : April 12, 2022 |
| INVENTOR(S) | : Malik Y. Kahook et al. |

It is certified that error appears in the above-identified patent and that said Letters Patent is hereby corrected as shown below:

In the Claims

- Claim 1, Column 17, Line 31, delete "lens (24)" and replace with --lens--.

- Claim 1, Column 18, Line 2, delete "lens (24)" and replace with --lens--.

- Claim 6, Column 18, Lines 26-27, delete "lens (24)" and replace with --lens--.

Signed and Sealed this
Twenty-ninth Day of November, 2022

*Katherine Kelly Vidal*

Katherine Kelly Vidal
*Director of the United States Patent and Trademark Office*